United States Patent
Douroumis et al.

(10) Patent No.: US 11,246,833 B2
(45) Date of Patent: Feb. 15, 2022

(54) METHOD OF PRODUCING A GRANULATED COMPOSITION

(71) Applicants: Cubic Pharmaceuticals Ltd., Kent (GB); Delta Pharmaceuticals Ltd., Kent (GB)

(72) Inventors: Dennis Douroumis, Kent (GB); Mohammed Maniruzzaman, Kent (GB); Saumil Kiritkumar Bhatt, Kent (GB); Anwar Ali, Kent (GB); Arun Jangra, Kent (GB)

(73) Assignees: Cubic Pharmaceuticals Ltd., Kent (GB); Delta Pharmaceuticals Ltd., Kent (GB)

( * ) Notice: Subject to any disclaimer, the term of this patent is extended or adjusted under 35 U.S.C. 154(b) by 146 days.

(21) Appl. No.: 15/549,880

(22) PCT Filed: Feb. 9, 2016

(86) PCT No.: PCT/GB2016/050293
§ 371 (c)(1),
(2) Date: Aug. 9, 2017

(87) PCT Pub. No.: WO2016/128726
PCT Pub. Date: Aug. 18, 2016

(65) Prior Publication Data
US 2018/0015040 A1    Jan. 18, 2018

(30) Foreign Application Priority Data

Oct. 8, 2015  (GB) ...................... 1517824

(51) Int. Cl.
| | |
|---|---|
| *A61K 9/14* | (2006.01) |
| *A61K 31/192* | (2006.01) |
| *A61K 9/20* | (2006.01) |
| *A61K 31/00* | (2006.01) |
| *B29B 9/00* | (2006.01) |
| *B29B 9/06* | (2006.01) |
| *B29B 9/12* | (2006.01) |

(52) U.S. Cl.
CPC .............. *A61K 9/143* (2013.01); *A61K 9/145* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 31/00* (2013.01); *A61K 31/192* (2013.01); *B29B 9/00* (2013.01); *B29B 9/06* (2013.01); *B29B 9/12* (2013.01)

(58) Field of Classification Search
CPC ...... A61K 9/143; A61K 9/145; A61K 9/2095; A61K 9/2054; A61K 9/2018; A61K 9/2013; A61K 9/2009; A61K 31/00; A61K 31/192; A61K 9/2027; B29B 9/00; B29B 9/06
See application file for complete search history.

(56) References Cited

U.S. PATENT DOCUMENTS

| | | | |
|---|---|---|---|
| 6,492,530 B1 * | 12/2002 | Albano | .................. A61P 35/00 548/455 |
| 2003/0203029 A1 | 10/2003 | Wong et al. | |
| 2005/0129774 A1 | 6/2005 | Morein et al. | |
| 2009/0175940 A1 | 7/2009 | Gruber | |
| 2010/0038816 A1 * | 2/2010 | Ghogh | ................. A61K 9/1641 264/176.1 |
| 2012/0053248 A1 * | 3/2012 | Kolter | .................. A61K 31/496 514/772.6 |
| 2012/0231083 A1 | 9/2012 | Carley et al. | |

FOREIGN PATENT DOCUMENTS

| | | |
|---|---|---|
| EP | 0336014 | 10/1989 |
| WO | WO-2000038655 | 7/2000 |
| WO | WO-2003080029 | 10/2003 |
| WO | WO-2010050897 | 5/2010 |
| WO | WO-2010100414 | 9/2010 |
| WO | WO-2011154009 | 12/2011 |
| WO | WO-2014013044 | 1/2014 |

OTHER PUBLICATIONS

Kinoshita, M. et al., Improvement of Solubility and Oral Bioavailability of a Poorly Water-Soluble Drug, TAS-301, by its Melt-Adsorption on a Porous Calcium Silicate, Journal of Pharmaceutical Sciences, 91(2): 362-370, Feb. 2002.

Kinoshita, M. et al., Highly Stabilized Amorphous 3-bis(4-Methoxyphenyl)methylene-2-indolinone (TAS-301) in Melt-Adsorbed Products with Silicate Compounds, Drug Development and Industrial Pharmacy, 29(5): 523-530, 2003.

MacLean, J. et al., Manufacture and Performance Evaluation of a Stable Amorphous Complex of an Acidic Drug Molecule and Neusilin, Journal of Pharmaceutical Sciences, 100(8): 3332-3344, 2011.

Maniruzzaman, M. et al., One-step continuous extrusion process for the manufacturing of solid dispersions, International Journal of Pharmaceutics, 496: 42-51, 2015.

Schrank, S. et al., Ibuprofen-Loaded Calcium Stearate Pellets: Drying-Induced Variations in Dosage Form Properties, AAPS PharmSciTech, 13(2): 686-698, 2012.

(Continued)

*Primary Examiner* — Robert S Cabral
(74) *Attorney, Agent, or Firm* — Julie K. Staple; Dinsmore & Shohl LLP

(57) ABSTRACT

A method of producing an extruded, powdered/granulated composition comprising an active pharmaceutical ingredient (API), by the steps of providing an API and a porous inorganic excipient, and processing them by an extrusion process to directly produce an extruded, powdered/granulated composition wherein the API is at least partially absorbed within the pores of the inorganic excipient. In preferred embodiments, the API is melted, or solubilised in a solubilizer.

16 Claims, 17 Drawing Sheets

(56) References Cited

OTHER PUBLICATIONS

Wang, Z. et al., Increasing the oral bioavailability of poorly water-soluble carbamazepine using immediate-release pellets supported on SBA-15 mesoporous silica, International Journal of Nanomedicine, 7: 5807-5818, 2012.

Maniruzzaman, M. et al., Poster No. W5235, Neusilin®-Polymer Extrudates for the Developments of Solid Dispersions, Final Program and Exhibit Guide, 2013 AAPS Annual Meeting and Exposition, Nov. 10-14, 2013.

Communication pursuant to Rule 114(2) EPC, European Patent Application No. 16709488.7, dated Jun. 1, 2021.

Maniruzzaman, M. et al., Continuous twin-screw granulation for enhancing dissolution of poorly water soluble drug, International Journal of Pharmaceutics, 496: 52-62, Sep. 18, 2015.

Communication pursuant to Rule 114(2) EPC, European Patent Application No. 16709489.5, dated Jun. 1, 2021.

\* cited by examiner

METHOD OF PRODUCING A GRANULATED COMPOSITION

FIELD OF THE INVENTION

The invention relates inter cilia to a method of producing an extruded, powdered/granulated composition comprising an active pharmaceutical ingredient (API), a method of producing a pharmaceutical tablet containing the same together with products derived therefrom.

BACKGROUND TO THE INVENTION

Hot-melt extrusion (HME) has been used in a wide range of manufacturing processes. Aside from its use in the plastics, rubber and food manufacturing sectors, HME has been used in the manufacture of pharmaceutical dosage forms e.g. tablets or films. In general terms, HME involves pumping a mixture of raw materials at controlled (often elevated) temperature and/or pressure through a barrel to produce a composition that is forced out of the barrel through a die. The raw materials are typically fed into the extruder (the extruder barrel) via a hopper. Flow through the barrel is usually associated with mixing, grinding, compressing, kneading and/or venting. Within the barrel are typically one or two rotating screws (corotating or counter rotating).

Initial extruded compositions (extrudates) usually require further down steaming processing before final use, for example into powders for tabletisation, e.g. tablet compression, in the field of pharmaceuticals. However, many prior art extrusion methods (especially where Ibuprofen is extruded) result in sticky extrudates that require cryo-milling for powder formation. Cryo-milling is a time consuming and costly processing step that inhibits the scale-up of such processes to an industrial operation. Other resource-consuming, post-extrusion processing steps can include cooling, cutting, pelletising and micronisation.

It is amongst the objects of the present invention to attempt a solution to this problem (i.e. to improve the speed and efficiency with which a powdered/granulated extrudate can be formed), and to improve various characteristics of extrudates (and pharmaceutical form derived therefrom) for pharmaceutical use, such as improved drug-loading, stability and taste-masking and, in the case of tablet forms in particular, increased disintegration rate, increased hardness and decreased friability.

SUMMARY OF THE INVENTION

Accordingly, the invention provides a method of producing an extruded, powdered/granulated composition comprising an active pharmaceutical ingredient (API), said method comprising the steps of:
(a) providing an API;
(b) providing a porous and particulate inorganic excipient; and
(c) processing (a) and (b) by a twin screw extrusion granulation process to directly produce an extruded, powdered/granulated composition wherein the API is, absorbed within the pores of the carrier particles.

In one embodiment, step (c) comprises partially or fully melting the API. Preferably m such embodiments, step (c) is carried out in the absence of a solvent.

In one embodiment, the method comprises partially or fully solubilising the API in a solubilizer, e.g. in step (c). Preferably in such embodiments, step (c) is carried out without heating. For example, step (c) is carried out at room temperature, e.g. from about 20° C. to about 30° C.

Preferably, in any of the above methods, step (c) occurs in an extrusion barrel without an extrusion die.

In preferred embodiments the API is hydrophobic, preferably wherein the AI has solubility of 20 mg/ml or less. Preferably, the API is selected from ibuprofen, Indomethacin, Lamotridine, Diazepam, Griseofulvin, Progesterone, 17 beta-estradiol, Furosemide, Gliclazide, Glipiciide. Aceclofenac, Ketoprofen, Diclofenac, Felodipine, Morphine, Naproxone, Nimodipine, Ofloxacin, Curcumin, Paclitaxel, and Cisplatin. More preferably the API is ibuprofen or indomecthacin, most preferably ibuprofen.

In preferred embodiments, the inorganic excipient has a specific surface area of more than 100 $m^2/g$ and/or a Carr Index of less than 18.

Preferably the inorganic excipient is selected from the group consisting of:
A magnesium phosphate
An iron pyrophosphate (preferably ferric)
An iron orthophosphate (preferably ferric)
A sodium phosphate
A potassium phosphate
A calcium phosphate
Silicon dioxide
Magnesium stearate
Tricalciumphosphate
Silica
Hydrated Silica
Alumina Magnesium Metasilicate
Alumina Magnesium Metasilicate
Aluminium Calcium Sodium Silicate
An aluminium silicate
An iron silicate In one embodiment, the inorganic excipient is a metal aluminosilicate.

The most preferred inorganic excipients are:
Magnesium Alumino-metasilicate ($Al_2O_3.MgO.1.7SiO_2.xH_2O$)
$SiO_2$
Dibasic calcium phosphate (anhydrous)($CaHPO_4$)

Also provided is a powered/granulated composition obtainable/obtained by any of the above methods.

Provided is a powdered/granulated composition comprising an API that is at least partially absorbed within the pores of a porous inorganic excipient. Preferably, the API and/or the inorganic excipient is as defined above with respect to the provided methods.

Also provided is a pharmaceutical composition, such as a capsule or a tablet, comprising a powdered/granulated composition as described herein and one or more additional pharmaceutically acceptable excipients. For example, the pharmaceutical composition may be a tablet, such as a direct compression tablet and/or an oral-dissolvable tablet.

Additionally provided is a tablet, preferably an oral-dissolvable tablet (ODT), comprising any one of the compositions mentioned above. Alternatively is provided a tablet, preferably a direct compression tablet, more preferably an oral-dissolvable direct compression tablet, comprising any one of the composition mentioned above.

In one embodiment, the method comprises the further steps:
(d) blending the extruded, powdered/granulated composition with one more pharmaceutically acceptable excipients to produce a composition blend; and
(e) directly compressing the composition blend into a direct compression tablet.

Additionally provided is a direct compression tablet obtainable/obtained from the method described above. Preferably, the tablet is an oral-dissolvable tablet (ODT).

Also provided is a method of producing an extruded, powdered/granulated composition comprising an active pharmaceutical ingredient (API), said method comprising the steps of:
(a) providing an API;
(b) providing a porous and particulate inorganic excipient; and
(c) processing (a) and (b) by an extrusion process to directly produce an extruded, powdered/granulated composition wherein the API is absorbed within the pores of the carrier particles.

Also provided is a powered/granulated composition obtainable by any of the above methods.

Provided is a powdered/granulated composition comprising an API that is at least partially absorbed within the pores of a porous inorganic excipient. Preferably, the API and/or the inorganic excipient is as defined above with respect to the provided methods.

Additionally provided is a tablet (preferably an oral-dissolvable tablet (ODT) comprising any one of the compositions mentioned above.

Included within the scope of the invention is a method of producing an extruded, powdered/granulated composition, a method of producing a tablet, a powdered/granulated composition and a tablet substantially as described herein.

BRIEF DESCRIPTION OF FIGURES

FIG. 6 shows XRPD diffractograms for the sample of Example 10 stored for 1 month, 1 year, and 1.5 years, together with XRPD diffractograms of pure DCPA and ibuprofen.

DETAILED DESCRIPTION OF THE INVENTION

Figure 1:
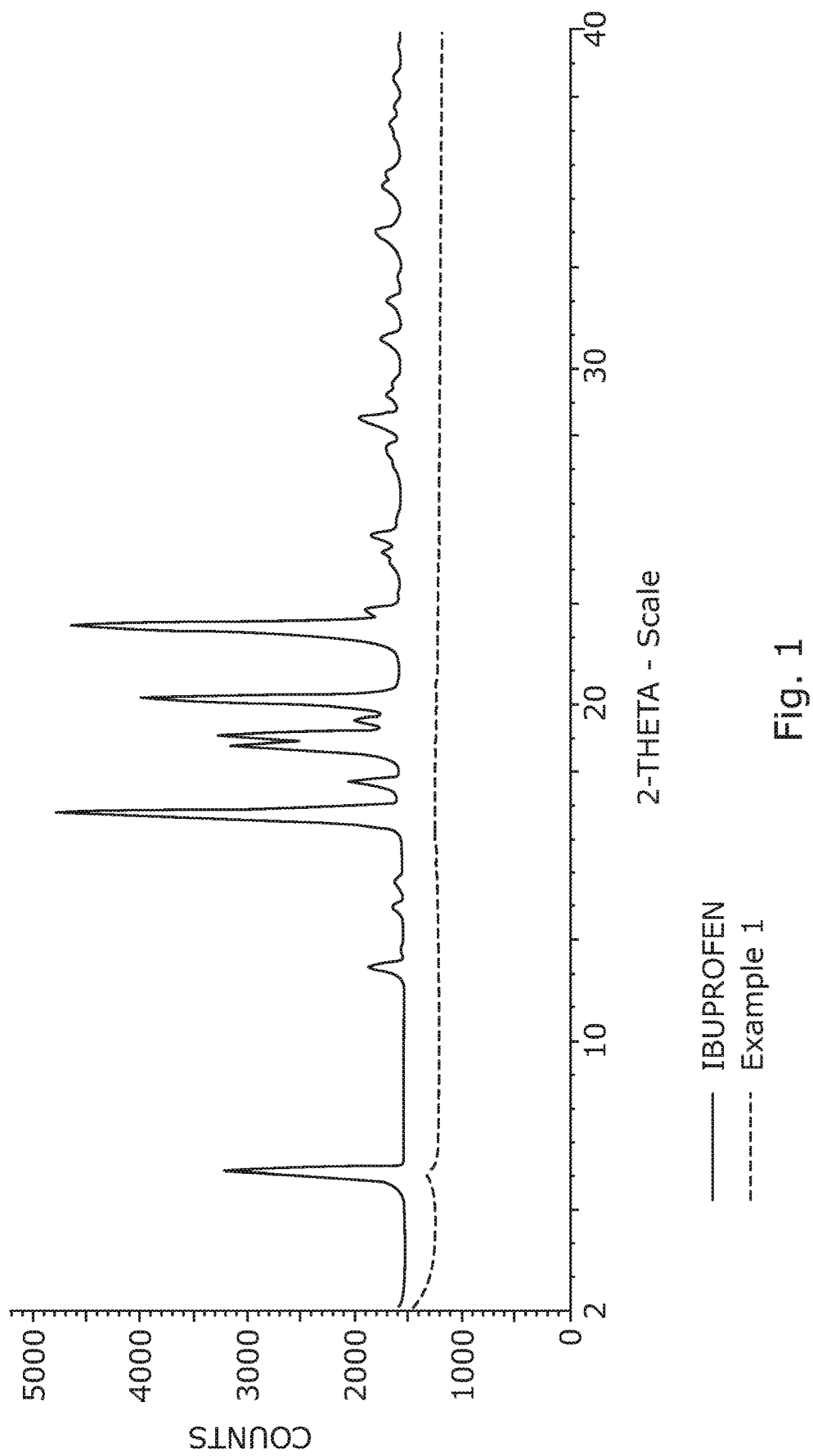
FIG. 1 shows XRPD diffractograms of pure ibuprofen and one of the example extrudates (Example 1).

The invention relates to a method of producing an extruded, powdered/granulated composition comprising an active pharmaceutical ingredient (API).

The term a "powdered/granulated composition" refers to a composition that is powdered and/or granulated. For example, this may refer to a powdered composition, a granulated composition, or a powdered granulated composition.

An API includes any compound that has a biological effect and includes particularly a compound that can prevent or treat a disease, condition or symptom in a human or animal body. Of particular interest is any API that is hydrophobic, for example an API having a water solubility (e.g. at 25° C.) of 20 mg/ml or less, such as 15 mg/ml or less, 10 mg/ml or less, or 5 mg/ml or less. Particularly preferred APIs include those in Classes II and IV of the Biopharmaceutical Classification system (also known as the Biopharmaceutics Classification System)—BCS.

According to the BCS, APIs are classified as follows:
Class I—High Permeability, High Solubility
Class II—High Permeability, Low Solubility
Class III—Low Permeability, High Solubility
Class IV—Low Permeability, Low Solubility An API is considered HIGHLY SOLUBLE when the highest dose strength is soluble in <250 ml water over a pH range of 1 to 7.5.

A drug substance is considered HIGHLY PERMEABLE when the extent of absorption in humans is determined to be >90% of an administered dose, based on mass-balance or in comparison to an intravenous reference dose.

Class II and Class IV APIs therefore have a Low Solubility, such that the highest required dose strength is not soluble in less than 250 ml water over the pH range 1 to 7.5. Suitable APIs may have high or low permeability.

Particularly-preferred APIs are: Ibuprofen, Indomethacin, Lamotridine, Diazepam, Griseofulvin, Progesterone, 17 beta-estradiol, Furosemide, Gliclazide, Glipizide, Aceclofenac; Ketoprofen, Diclofenac, Felodipine, Morphine, Naproxone, Nimodipine, Ofloxacin, Curcumin, Paclitaxel, and Cisplatin.

Especially preferred APIs are Ibuprofen and Indomethacin.

If the API is ibuprofen—(RS)-2-(4-(2-methylpropyl)phenyl)propanoic acid (as is preferred herein)—this can be in the form of a racemate or either of the S- or R-enantiomer. The acid and pharmaceutical salt forms are contemplated. The API is preferably present in the extrudate and/or pharmaceutical forms thereof at at least 10% w/w, such as 10-60% w/w, more preferably 20-50% w/w, such as, for the extrudates, at least 35% w/w, preferably 35-45% w/w (e.g.

40% w/w) and, for the pharmaceutical forms, at least 25% w/w, preferably 25-35% w/w (e.g. 30% w/w).

In the claimed method a porous and particulate inorganic excipient is provided (e.g. a pharmaceutically-acceptable inorganic excipient). In particular, the inorganic excipient should preferably have the following features:

Heat Stability: The inorganic excipient should be heat-stable at the temperatures used for the process. For example, if the API is ibuprofen, this degrades above approximately 152° C., the inorganic excipient should be stable to at least this temperature. Indomethacin is more heat stable—up to approximately 230° C., and the inorganic excipient should therefore be stable to at least this temperature. Most inorganic excipients are, of course, heat-stable to a much higher degree.

Physical Form: The inorganic excipient should be in a powder or granular form. Particles should preferably have a particle size of less than about 500 microns, for example in the range of about 40-500 microns.

Specific Surface Area: The inorganic excipient should be porous, and have a high specific surface area (SSA) to allow interaction with other components in the composition. Preferably, the SSA should be at least 100 $m^2/g$, or at least 300 $m^2/g$, or at least 300 $m^2/g$, or at least 500 $m^2/g$ or at least 800 $m^2/g$. Excipients having an SSA of between 100-800 $m^2/g$, such as between 200-300 $m^2/g$, are particularly preferred.

Loss on Drying: The inorganic excipient should exhibit low loss on drying, and should lose less than 20%, preferably less than 15%, or 10%, or 5%, or 2%, or most preferably less than 1% weight on drying at 110° C. for 7 hr.

Angle of Repose: To give good handling properties, excipients having an angle of repose of between 25°-45° are particularly preferred.

Flowability: The inorganic excipient should exhibit good flow properties. This may be measured using the Carr Index (a measurement known in the pharmaceutical industry for measurement of compressibility and flowability). An excipient having a Carr Index of less than 18, or less than 17 or 16 is preferred. Particularly preferred are excipients having a Carr Index of less than 15, for example between 5-15.

The following inorganic excipients are envisaged as being appropriate for use:

A magnesium phosphate
An iron pyrophosphate (preferably ferric)
An iron orthophosphate (preferably ferric)
A sodium phosphate
A potassium phosphate
A calcium phosphate
Silicon dioxide
magnesium stearate
Tricalciumphosphate
Silica
Hydrated Silica
Alumina Magnesium Metasilicate
Alumina Magnesium Metasilicate
Aluminium Calcium Sodium Silicate
An aluminium silicate
An iron silicate Particularly preferred excipients are the amorphous form of Magnesium Alumino-metasilicate ($Al_2O_3.MgO.1.7SiO_2.xH_2O$), $SiO_2$ and dibasic calcium phosphate anhydrous ($CaHPO_4$), commonly known as DCPA.

Once the API and carrier are provided, they are preferably mixed (e.g. to homogeneity) before being subjected to an extrusion process, whereby the components are passed along and out of an extrusion barrel, whilst being subject to heating. Preferably, the barrel does not have an extrusion die. In the claimed method this extrusion leads directly to an extruded, powdered/granulated composition wherein the API is absorbed within the pores of the carrier particles. This means that the extrudate exits the barrel as a powder, and that no processing (e.g. cutting/micronisation/cryo-milling) of the extrudate is required after it exits the barrel to produce a powder. The claimed method, therefore, provides a fast and efficient way of producing an extruded, powdered/granulated composition comprising an API, without requiring the use of resource-consuming, post-extrusion processing such as cooling, cutting, pelletising, micronisation or cryo-milling. (And in preferred embodiments, therefore, the claimed method does not comprise any one or any combination of these processes.)

The porous and particulate carrier used in the invention absorbs within its pores, or adsorbs at its surface, at least a portion (and potentially all) of the API, either in its molten or partially molten (at least softened) form, or as a solution with a solubiliser. (in this context, solution should be taken to include a true solution, or a surfactant-stabilised dispersion of the API within a liquid solubiliser.)

In order to absorb the API in this way, the carrier has pores, some of which at least are open to the exterior surface of the carrier particles. In some embodiments, the API might be only partially absorbed into the interstices of the carrier, with some of the API remaining at the surface. In other embodiments, all of the API will be taken into the interstices of the carrier. The degree to which the API will be taken into the carrier will depend on factors such as the viscosity and surface tension of the molten or solubilised API and the surface characteristics and pore sizes of the carrier. These may be controlled by varying processing characteristics such as temperature (to influence e.g. the viscosity) or by choice of solubiliser or carrier particle characteristics.

Preferably at least 30% of the API is absorbed into the pores, or adsorbed onto the surface, of the inorganic excipient. More preferably, at least 40%, 50%, 60%, 70%, 80%, 90%, 95%, 98% or even 100% of the API is so absorbed or adsorbed.

By powder (or powdered composition), it is meant e.g. that the material is in the form of fine, discrete particles. Such a powder will typically have an average particle size of less than about 1 mm diameter (i.e. will pass through a 1 mm mesh), and preferably less than about 600 μm, or less than about 500 μm or less than about 300 μm, or less than about 100 μm. Particularly preferred powders are those having a mean particle size of about 325 μm, e.g. a powder in which at least 90% (w/w) of the particles have a particle size of between 100 μm and 550 μm.

For embodiments in which a portion of the API remains at the surface of the carrier, either adsorbed onto the surface, or absorbed within a pore communicating with the surface, the presence of such surface-associated API can assist in binding individual carrier particles together to form granules, which can improve the handling characteristics of the particles. Examples of such granulation will be presented below.

The skilled person will be able to select appropriate processing parameters once the particular ingredients and extruder apparatus have been chosen. For example, especially for Ibuprofen, for making small batches, the extrusion process may be carried out in a Eurolab 16 mm Thermo-Fisher extruder with a screw speed rate of 100 to 200 rpm a feed rate of 4 to 5 kg/hr. Preferably, a twin screw extruder is used. The process may be scaled up for larger scale production by routine experimentation and industry scale-up methodologies.

The extrusion process provides further mixing, heat, and shear forces that act to break up the particulate material in the inlet.

In preferred embodiments, the extrusion process of the claimed method comprises partially or fully melting the API. This can occur at a temperature ranging from ambient (e.g. 20-30° C., such as 25° C.) up to or including the melting point of the API, or up to the boiling point of the API. For example (and particularly where the API is Ibuprofen), extrusion is preferably carried out above e.g. 25° C., 30° C. or 35° C., such as at 60° C. or at 70° C. (below the inciting point of 75-78° C.) or at temperatures above the melting point, such as 140° C. (below the boiling point of 157° C.) or at a temperature between 60° C. or 70° C. and 140° C.

Preferably, the extrusion temperature is reduced to ambient (temporally or spatially) prior to exit of the composition from the extruder barrel. In such embodiments, the screw speed is preferably 100 to 150 rpm.

In alternative, preferred embodiments, the claimed method comprises partially or fully solubilising the API in a solubiliser. The solubilizer should preferably be selected to be liquid at room temperature and have a boiling or flash point between 100-200° C., The degree of solubility will, of course depend on the specific API being processed, and it is preferable to select a solubilizer such that the solubility of the API is at least 50 mg API per ml of solubilizer, and preferably at least 75, 100, 125 or 150 mg API per ml of solubilizer, Routine experimentation may be used to select an appropriate solubilizer for any particular API.

When solubilizers are used in the method, they can act to decrease the apparent melting point of the API, thereby allowing a processing temperature at below the melting point of the pure API. This phenomenon is described below.

Generally, appropriate solubilizers can include glycerides, fatty acids, fatty alcohols, glycols and derivatives thereof.

Particularly preferred solubilizers may be selected from the group consisting of liquid polyethylene glycol; propylene glycol; liquid fatty alcohols with at least 8 carbon atoms; liquid polyethoxylated fatty acids; liquid PEG glycerol fatty acid esters; liquid ethers of polyethylene glycol; sorbitan fatty acid esters; polyoxyethylene sorbitan monooleate; and alkyl alcohols. Most preferably, they are selected from the group consisting of polysorbate; glycerol; liquid polyethylene glycol; PEG (polyethylene glycol) esters (with glyceride fraction); sorbitan fatty acid esters and propylene glycol.

In such embodiments, (e.g. where where a Eurolab 16 mm Thermo-Fisher extruder is used) the screw speed is preferably 150 to 200 rpm and extrusion can occur at a temperature ranging from ambient (e.g. 20-30° C., such as 25° C.) up to or including the melting point of the API, or up to the boiling point of the API. The process may be scaled up for larger scale production (e.g. by choice of extruder dimensions, screw speed and feed rate) by routine experimentation and industry scale-up methodologies.

For example (and particularly where the API is Ibuprofen), extrusion is preferably carried out above e.g. 25° C., 30° C. or 35° C., such as at 60° C. or at 70° C. (below the melting point of 75-78° C.) or at temperatures above the melting point, such as 140° C. (below the boiling point of 157° C.), or at a temperature between 60° C. or 70° C. and 140° C.

Preferably, the extrusion temperature is reduced to ambient (temporally or spatially) prior to exit of the composition from the extruder barrel. In such embodiments, the screw speed is preferably 100 to 150 rpm.

It is especially preferred that the processing, takes place at below the boiling point of the solubilizer.

The method of the invention does not require the use of a polymer. In preferred embodiments therefore (to reduce cost and avoid problems such as stickiness that can sometimes occur when polymers are used in conventional HME), a polymer (e.g. a pharmaceutically-acceptable polymer that might be normally used in a melt extrusion process, and exhibiting melting or softening behaviour, with a glass transition temperature -$T_G$- below the maximum operating temperature of the process), such as a hydrophilic polymer, is not used in the production method (and e.g. such a polymer is present in the composition of the invention at less than 10% w/w, preferably less than 5% w/w, preferably less than 1% w/w, preferably less than 0.1% w/w, and is most preferably absent).

The compositions of the invention can be incorporated into pharmaceutical forms for administration of the API to an individual in need thereof, such as solid forms (e.g. tablets and films and the like). A particular form of interest is a tablet for e.g. oral-enteral delivery. In particularly preferred embodiments the claimed tablet is an orally-dissolvable tablet (ODT), a tablet configured to disintegrate and/or dissolve in the mouth (e.g. on or under the tongue), for instance upon contact with saliva, prior to swallowing. Advantages of an ODT formulation include increased compliance (especially in individuals with dysphagia) and more rapid API absorption.

In order to produce an ODT, it preferable that pharmaceutically-acceptable disintegrants are incorporated into the tablet composition.

In preferred embodiments, the claimed tablet has a hardness of 5 kilopond (lip) or more, preferably 8 Kp or more, and/or a friability of 1% or less, such as 0.8% or less, preferably 0.6% or less, preferably 0.4% or less, preferably 0.2% or less, most preferably 0.1% or less, and/or an in vivo disintegration time (as measured by the protocol herein) of 30 s or less or 25 s or less, preferably 20 s or less, more preferably 15 s or less, most preferably 10 s or less, and/or an in vitro disintegration time (as measured by the protocol herein) of 25 s or less or 20 s or less, preferably 15 s or less, more preferably 10 s or less, most preferably 5 s or less.

The tablets/ODTs of the present invention show comparable or improved characteristics compared with prior art products in terms of API loading, taste-masking and stability, and tablet hardness, friability and disintegration time.

Also provided is a continuous manufacturing process comprising a method described herein. Generally, in a continuous manufacturing process via a twin screw extrusion system, feeding of the input materials or mixtures (also known as starting materials such as blends of API and inorganic excipients) and the evacuation of processed output materials take place concurrently in a continuous mode. In a fully automated continuous manufacturing process controlled/automated by software, different steps involved in the processing of the extrudates and the finished products (e.g. tablets) are coordinated to form a continuous, production flow. The finished product collection occurs simultaneously in the continuous flow preferably at the optimised rate as the feeding of the starting materials in the feeding stations.

Please note that wherever the term 'comprising' is used herein we also contemplate options wherein the terms 'consisting of' or 'consisting essentially of' are used instead.

EXAMPLES

Example A—Ibuprofen

For each Example extrusion, ibuprofen (base, racemate) powder was mixed thoroughly with the other ingredients for 10 min using a Turbula TF2 mixer (Basel, Switzerland) to form a homogeneous blend prior to processing.

In all examples, the resultant blends were extruded a) at a temperature of 70° C. using a screw speed of 100 to 150 rpm orb) at a temperature of 140° C. using a screw speed of 150 to 200 rpm. In all cases a EuroLab 16 twin screw extruder (ThermoFisher, Germany) was used, with a feed rate of 4 to 5 kg/h. Extrudates were collected as free-flowing powders (directly from the barrel, without passing through a die).

ODT batches were then prepared using batch sizes of 100 g. All powdered/granulated extrudates were passed through a mesh sieve with an aperture of 500 μm before use. The batches were blended with sodium stearyl fumarate (1%) or magnesium stearate/silicon dioxide (0.8%/0.2%) in a Turbula TF2 mixer (Basel, Switzerland) for 10 minutes. Routine experimentation can be used to determine appropriate mixing regimes for particular formulations used, or where the process is sealed up.

Blends were directly compressed on a Flexitab trilayer tablet press (Oystar Martesty, Germany) using 13 mm normal flat punches. Dwell time was set at 30 ms and the compaction force varied from 8-12 kN to obtain tablets of about 3 mm thickness (average weight 600 to 630 mg). ODTs were further evaluated to characterise their properties. Please note that all prepared ODTs were stable under ICH storage conditions and showed effective taste masking. The ODTs showed particularly high hardness, low friability and rapid disintegration times.

All prepared tablets were evaluated for the uniformity of thickness, hardness (Erweka TBH 28, Frankfurt, Germany), friability (Erweka friabilator, model A3R, Frankfurt, Germany), and in vitro disintegration time.

In vitro disintegration time was measured for 6 tablets by inserting disks using 900 ml purified water at 37±2° C. in Disintegration Apparatus (Erweka, model ZT4, Heusenstamm, Germany) according to USP 27 NF 22 test. (United States Pharmacopoeia, National Formulary).

In vivo disintegration was performed by a panel of 6 healthy human volunteers from whom written consent was first obtained. The study is in accordance to the Code of Ethics of the World Medical Association (Declaration of Helsinki). The healthy volunteers of either sex (age 18-25) were selected, trained and the one tablet was held in the month after rinsing and the time required for complete disintegration of the tablet was recorded. The time when the tablet placed on the tongue disintegrated without leaving any lumps was taken as the end point.

Results

In the following table:

| | Chemical entity | Trade name | Ex. 1 | Ex. 2 | Ex. 3 | Ex. 4 | Ex. 5 | Ex. 6 |
|---|---|---|---|---|---|---|---|---|
| Extrudate Composition | Ibuprofen | — | 40 | 40 | 40 | 40 | 40 | 40 |
| | MAS | — | — | 10 | 20 | — | 30 | 35 |
| | DCPA | DICAFOS | 50 | 50 | 40 | 50 | 30 | 25 |
| | SiO₂ | — | 10 | — | — | — | — | — |
| | Lactose | — | — | — | — | 10 | — | — |
| | | Labrasol | — | — | — | — | — | — |
| | | Transcutol | — | — | — | — | — | — |
| | | Labrafil | — | — | — | — | — | — |
| | | Capryol | — | — | — | — | — | — |
| | Extrusion temperature (° C.) | | 70 | 70 | 70 | 70 | 140 | 140 |
| Tablet Composition | Extrudate from above | | 66.67 | 83.33 | 83.33 | 83.33 | 83.33 | 66.67 |
| | MCC | — | 12.33 | — | — | — | — | 17.33 |
| | XL 10 | — | — | — | — | — | — | — |
| | XL | — | 20 | 15.67 | — | — | 15.67 | 15 |
| | Vivasol | — | — | — | — | 15.67 | — | — |
| | Kollidon CL-SF | — | — | — | 15.67 | — | — | — |
| | Kollidon CL-MF | — | — | — | — | — | — | — |
| | SSF | PRUV | 1 | 1 | 1 | — | 1 | 1 |
| | MgSt | — | — | — | — | 0.8 | — | — |
| | SIO₂ | — | — | — | — | 0.2 | — | — |
| Results | Hardness (Kp) | | 11.0 | 9.0 | 11.0 | 10.5 | 9.5 | 10.5 |
| | Friability (%) | | 0.6 | 0.7 | 0.6 | 0.8 | 0.6 | 0.8 |
| | In vivo DT (s) | | 21 | 20 | 21 | 19 | 29 | 19 |
| | In vitro DT (s) | | 17 | 15 | 16 | 12 | 13 | 12 |

| | Chemical entity | Trade name | Ex. 7 | Ex. 8 | Ex. 9 | Ex. 10 | Ex. 11 | Ex. 12 |
|---|---|---|---|---|---|---|---|---|
| Extrudate Composition | Ibuprofen | — | 40 | 40 | 40 | 40 | 40 | 40 |
| | MAS | — | 25 | 40 | 20 | 10 | 50 | 50 |
| | DCPA | — | 35 | 20 | 40 | 50 | — | — |
| | SiO₂ | — | — | — | — | — | — | — |
| | Lactose | — | — | — | — | — | — | — |
| | | Labrasol | — | — | — | — | 10 | — |
| | | Transcutol | — | — | — | — | — | 10 |
| | | Labrafil | — | — | — | — | — | — |
| | | Capryol | — | — | — | — | — | — |
| | Extrusion temperature (° C.) | | 140 | 140 | 140 | 140 | 140 | 140 |
| Tablet Composition | Extrudate from above | | 79.11 | 79.11 | 83.33 | 66.67 | 83.33 | 83.33 |
| | MCC | — | — | — | — | 12.33 | — | — |
| | XL 10 | — | — | 19.88 | — | — | 15.67 | — |
| | XL | — | — | — | — | — | — | — |

-continued

| | | | | | | | | |
|---|---|---|---|---|---|---|---|---|
| | | Vivasol | — | — | — | 20 | — | 15.67 |
| | | Kollidon CL-SF | 19.88 | — | — | — | — | — |
| | | Kollidon CL-MF | — | — | 15.67 | — | — | — |
| | SSF | PRUV | 1 | 1 | 1 | 1 | 1 | 1 |
| | MgSt | | — | — | — | — | — | — |
| | $SiO_2$ | | — | — | — | — | — | — |
| Results | Hardness (Kp) | | 10.8 | 9.6 | 9.8 | 8.5 | 9.6 | 9.8 |
| | Friability (%) | | 0.6 | 0.9 | 0.6 | 0.8 | 0.8 | 0.7 |
| | In vivo DT (s) | | 22 | 29 | 15 | 23 | 13 | 18 |
| | In vitro DT (s) | | 15 | 22 | 13 | 15 | 8 | 11 |

| | Chemical entity | Trade name | Ex. 13 | Ex. 14 | Ex. 15 | Ex. 16 | Ex. 17 |
|---|---|---|---|---|---|---|---|
| Extrudate Composition | Ibuprofen | — | 40 | 40 | 40 | 40 | 40 |
| | MAS | — | 50 | 50 | — | — | — |
| | DCPA | — | — | — | 45 | 45 | 45 |
| | $SiO_2$ | — | — | — | — | — | — |
| | Lactose | — | — | — | — | — | — |
| | | Labrasol | — | — | 15 | — | — |
| | | Transcutol | — | — | — | 15 | — |
| | | Labrafil | 10 | — | — | — | 15 |
| | | Capryol | — | 10 | — | — | — |
| | Extrusion temperature (° C.) | | 140 | 70 | 140 | 70 | 70 |
| Tablet Composition | Extrudate from above | | 79.11 | 66.67 | 79.11 | 79.11 | 83.33 |
| | MCC | — | — | 12.33 | — | — | 15.67 |
| | | XL 10 | 19.88 | 20 | — | — | — |
| | | XL | — | — | — | 19.88 | — |
| | | Vivasol | — | — | — | — | — |
| | | Kollidon CL-SF | — | — | — | — | — |
| | | Kollidon CL-MF | — | — | 19.88 | — | — |
| | SSF | PRUV | 1 | 1 | 1 | 1 | — |
| | MgSt | | — | — | — | — | 0.8 |
| | $SiO_2$ | | — | — | — | — | 0.2 |
| Results | Hardness (Kp) | | 11.0 | 10.0 | 9.6 | 10.5 | 10.6 |
| | Friability (%) | | 0.8 | 0.4 | 0.8 | 0.2 | 0.1 |
| | In vivo DT (s) | | 22 | 20 | 8 | 19 | 18 |
| | In vitro DT (s) | | 16 | 12 | 4 | 12 | 11 |

All values are % w/w
DCPA = dibasic calcium phosphate acetate (anhydrous)
MCC = microcrystalline cellulose
MAS = amorphous form of Magnesium Alumino-metasilicate ($Al_2O_3 \cdot MgO \cdot 1.7SiO_2 \cdot xH_2O$)
MgSt = magnesium stearate
SSF = sodium stearyl fumarate (e.g. as sold under the RTM "PRUV")
DT = disintegration time; +/− 1 s in all cases
Hardness +/− 0.5 Kp in all cases Table of Chemical Designation of Trade Names

| Ingredients | Chemical Name |
|---|---|
| Labrasol | Caprylocaproyl macrogol-8 glycerides |
| Transcutol | Highly purified diethylene glycol monoethyl ether |
| Labrafil | Oleoyl macrogol-6 glycerides |
| Capryol | Propylene glycol monocaprylate (type II) |
| Xl 10 | Polyplasdone crossprovidone superdisintegrants |
| Xl | Polyplasdone crossprovidone superdisintegrants |
| Vivasol | Croscarmellose sodium |
| Kollidon Cl-SF | Crospovidone CL-SF |
| Kollidon Cl-MF | Crospovidone CL-MF |

Analysis and Characterisation of Extrudates and Tablets

The hardness, friability, in vivo and in vitro disintegration times were measured for each tablet. These results are presented at the bottom of the formulation table, above.

The extrudates produced by the claimed process were examined by X-Ray Powder Diffraction (XRPD), to determine the state of the ibuprofen in the products. FIG. 1 shows XRPD diffractograms of pure ibuprofen and one of the example extrudates (Example 1). The top trace shows the characteristic XRPD response of crystalline ibuprofen, the collection of peaks at 2-theta angles from about 16° to about 24° being good indicators of crystallinity. The peak at the 2-theta angle of approximately 6° is known to be also present in amorphous ibuprofen, and is likely to be due to the molecular structure of the compound rather than its higher order crystalline structure.

Corresponding traces for the extrudates of Example 1 shows virtually none of the crystallinity of the pure ibuprofen. In all samples, the degree of remaining crystallinity was determined (by analysis of the XRPD data) to be less than 15%, and in most cases, significantly lower than this, for example <10, <5% and even <2%.

It is believed that the movement of the API (in this case ibuprofen) into the pore structure of the inorganic carrier results in the formation of amorphous API, rather than the crystalline form.

Figure 2:
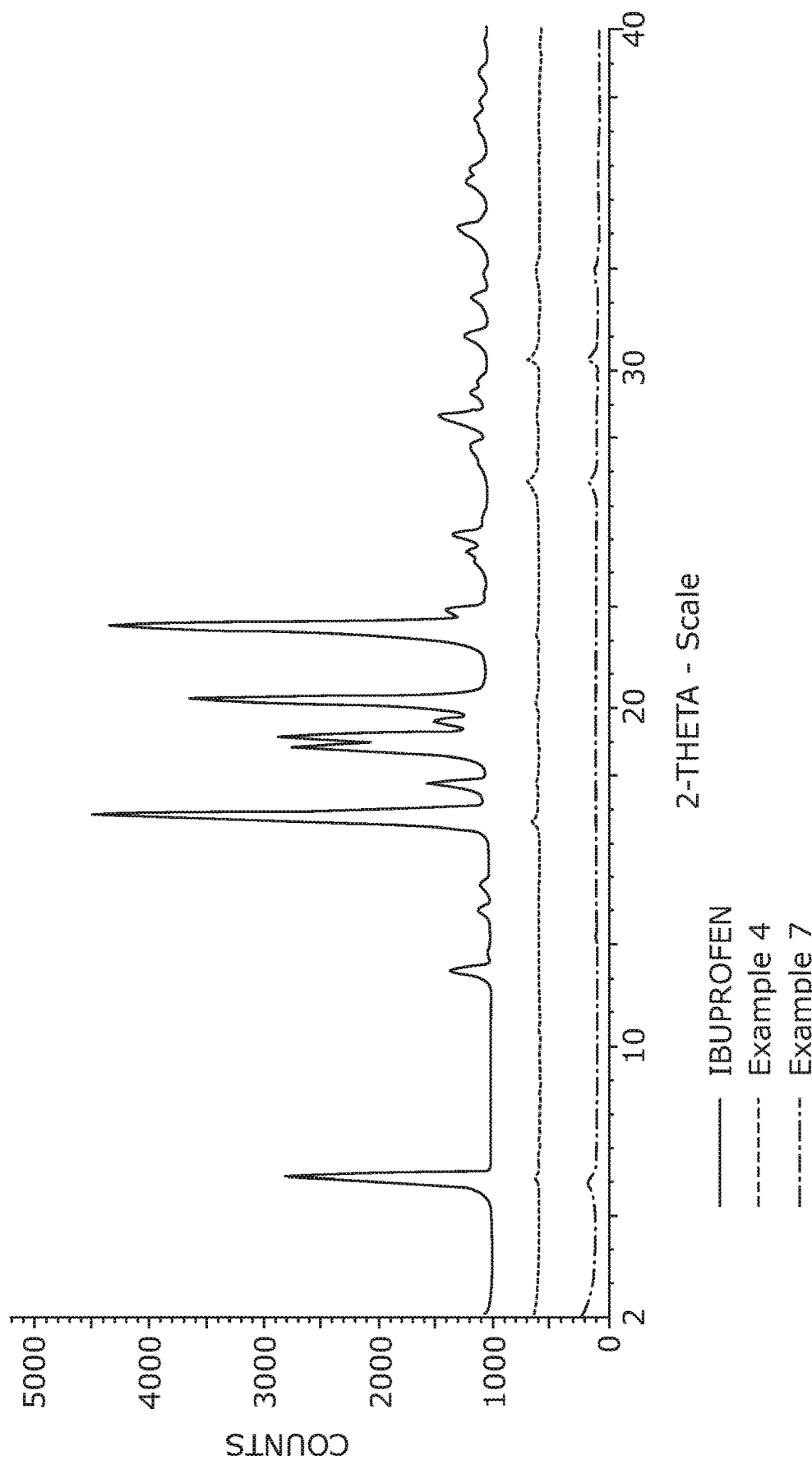
FIG. 2 shows XRPD diffractograms for the extrudates of Examples 4 and 7, together with that for pure ibuprofen, for reference.

FIG. 2 shows a diffractogram for the extrudates of Examples 4 and 7, together with that for pure ibuprofen, for reference. Again, it can be seen that virtually no crystallinity remains after processing.

Figure 3:
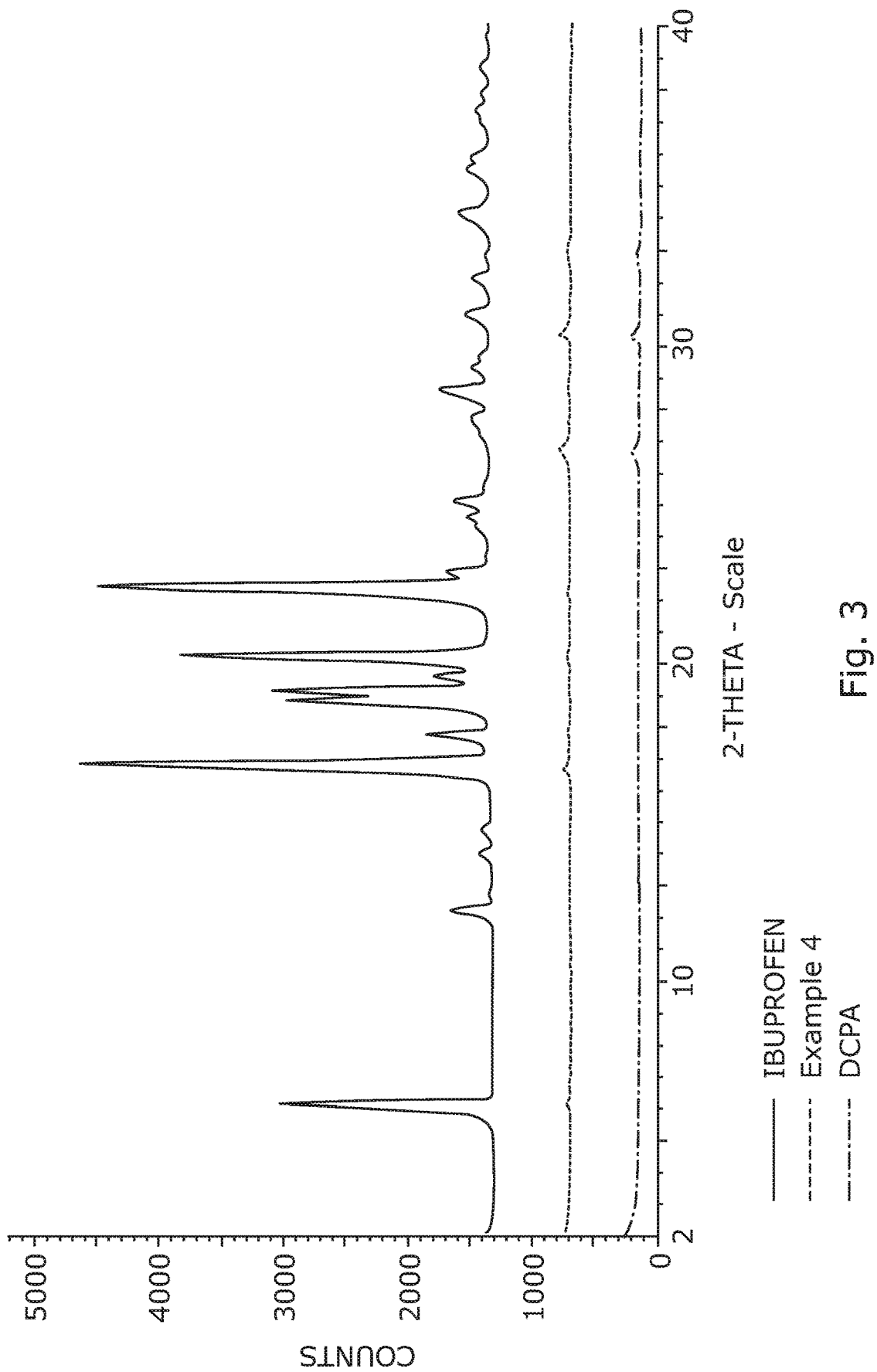
FIG. 3 shows XRPD diffractograms for the extrudate of Example 4, together with that for pure DCPA and pure ibuprofen, for reference.

FIG. 3 shows a diffractogram for the extrudate of Example 4, together with those of pure ibuprofen and pure DCPA. It can be seen that the characteristic peaks of ibuprofen have disappeared in the extrudate, indicating that the ibuprofen is an amorphous state, whereas the small, but characteristic peaks for DCPA at 2-theta angles of approximately 26.5° and 30° remain after processing.

Figure 4:
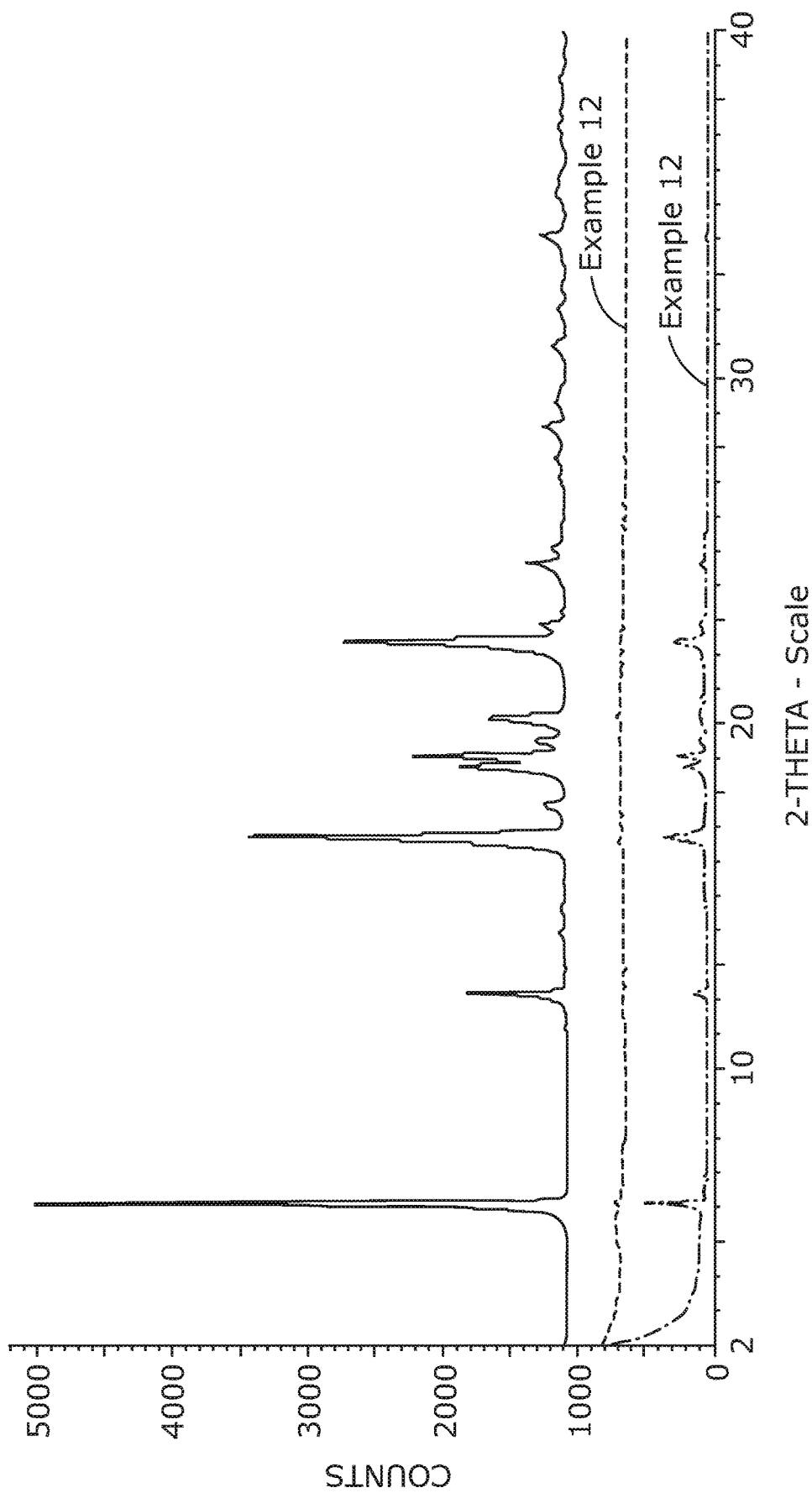
FIG. 4 similarly shows XRPD diffractograms for pure ibuprofen, the physical mix of ingredients before extrusion and the extruded product for Example 12.

FIG. 4 similarly shows diffractograms for pure ibuprofen, the physical mix of ingredients before extrusion and the extruded, product for Example 12. It can be seen that the characteristic peaks of crystalline ibuprofen are present in the physical mix, but that these all but disappear following extrusion, thereby indicating that virtually all of the ibuprofen is in amorphous form.

Figure 5:
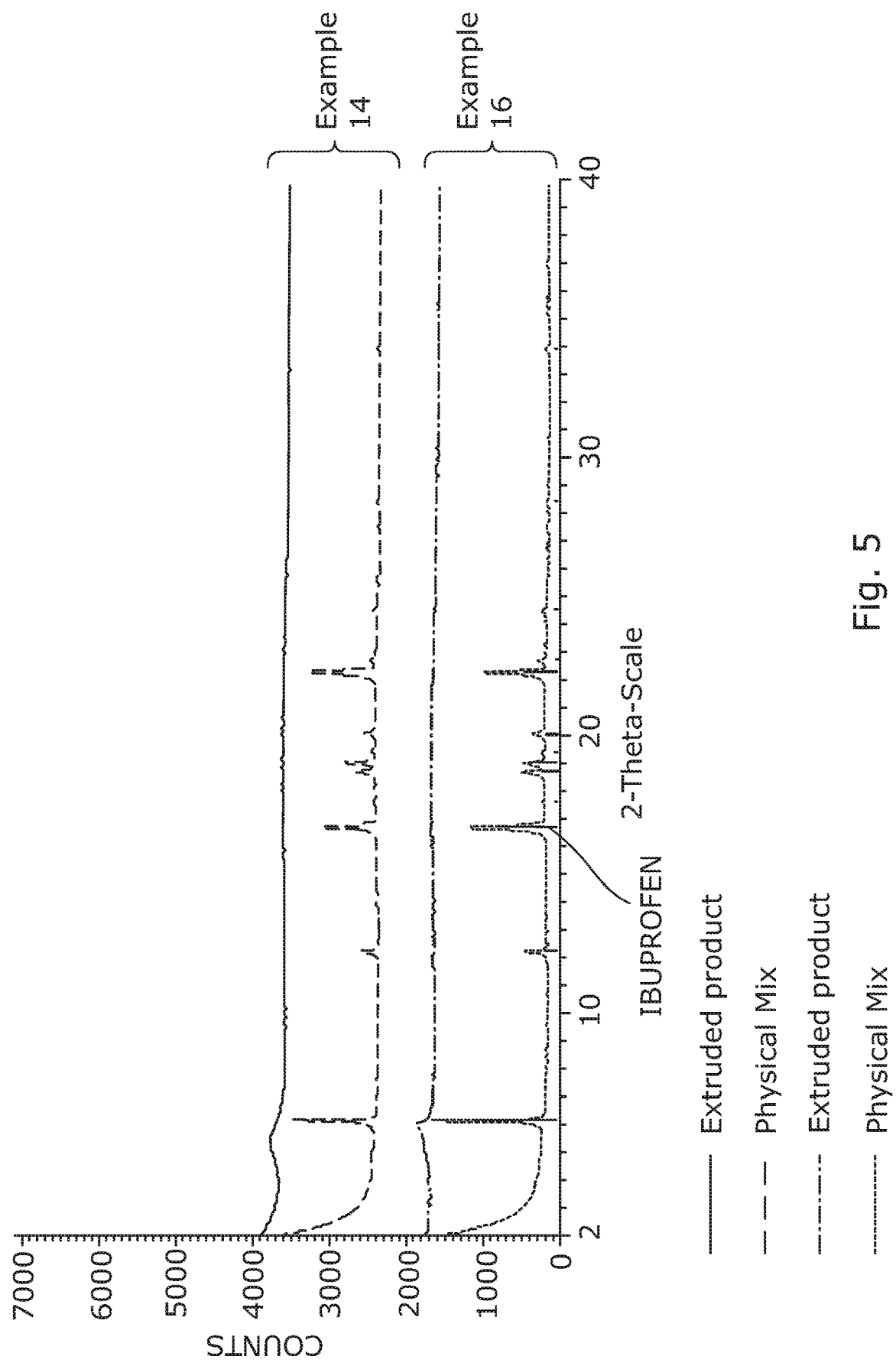
FIG. 5 show XRPD diffractograms for pure ibuprofen, the physical mix of ingredients before extrusion and the extruded product for Examples 14 and 16.

FIG. 5 show diffractograms for pure ibuprofen, the physical mix of ingredients before extrusion and the extruded product for Examples 14 and 16. Again, it can be seen that the characteristic peaks of crystalline ibuprofen are present in the physical mix, but that these all but disappear following extrusion, thereby indicating that virtually all of the ibuprofen in in amorphous form.

Figure 6:
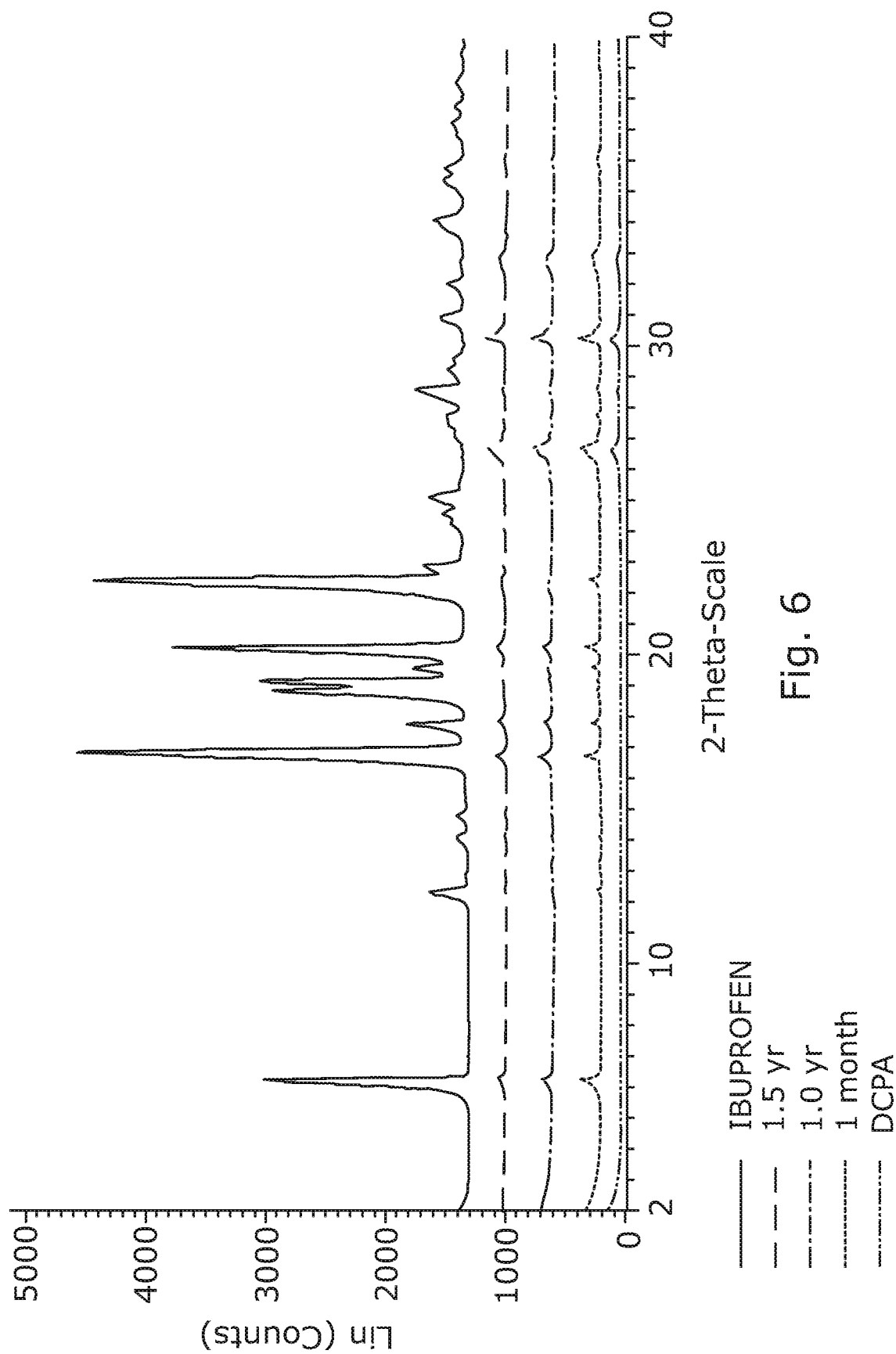
FIG. 6 show the results for a stability study conducted on the extrudate of Example 10. In particular.

Samples of extrudates were studied to determine their stability over long term storage. FIG. 6 show the results for such a study on the extrudate of Example 10. The diffractograms for pure ibuprofen and the inorganic carrier DCPA are shown at the top and bottom of the figure. Diffractograms of the extrudate after 1 month, 1 year, and 1.5 years are also shown. It can be seen that the processed extrudates show virtually none of the pure ibuprofen peaks, illustrating that the API is in predominantly an amorphous form; and the peaks do not change in size over the period of 1.5 years, indicating that no crystallisation has taken place on storage. The characteristic XRPD peaks for the excipient DCPA remain throughout the storage trial, and act as in internal control for the data.

Differential Scanning calorimetry (DSC) was used to further characterise the ingredients and the extrudates.

Figure 7:
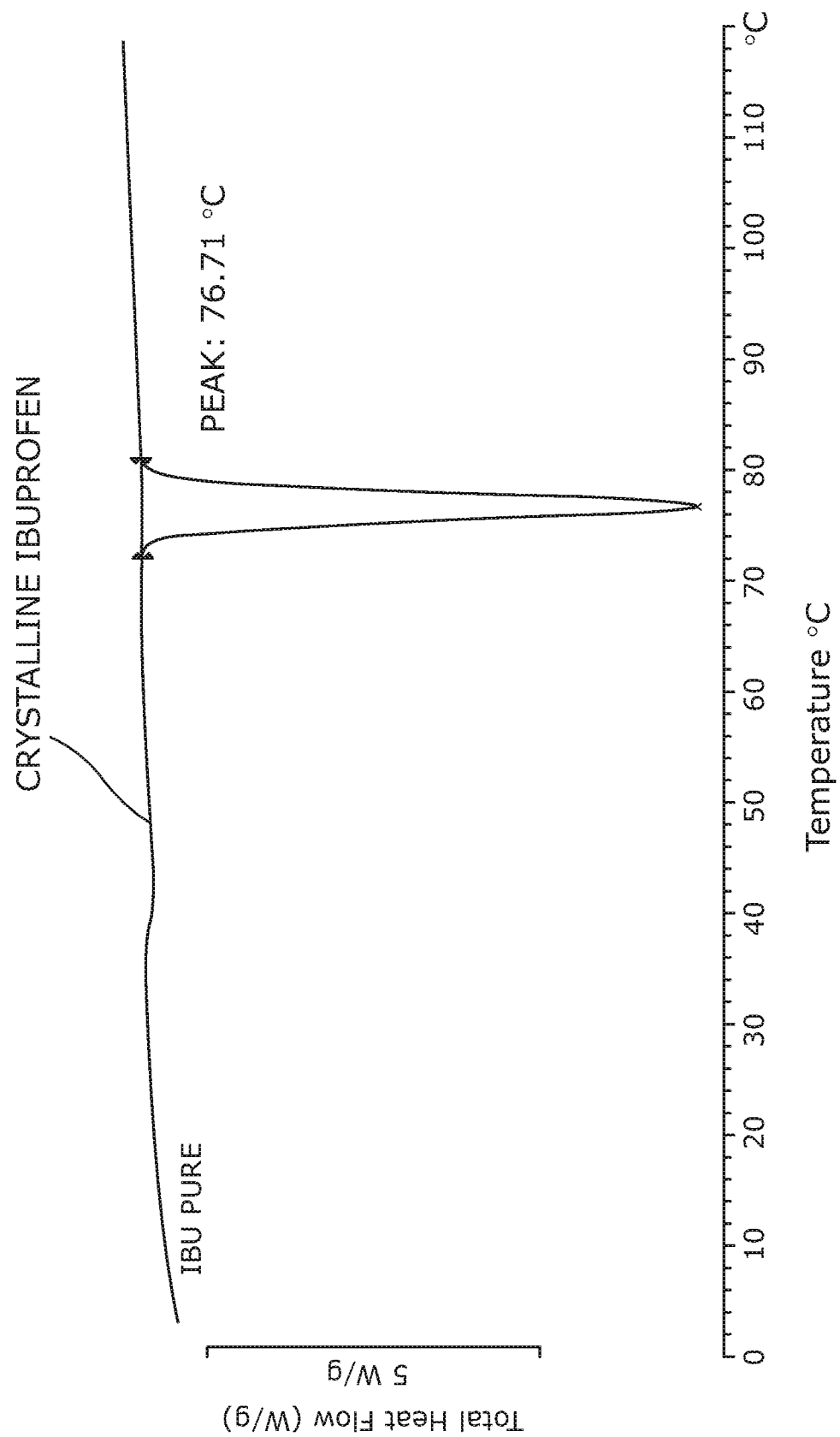
FIG. 7 show the DSC trace for pure crystalline ibuprofen.

FIG. 7 show the DSC trace for pure crystalline ibuprofen, indicating its melting temperature of approximately 76.7° C.

Figure 8:
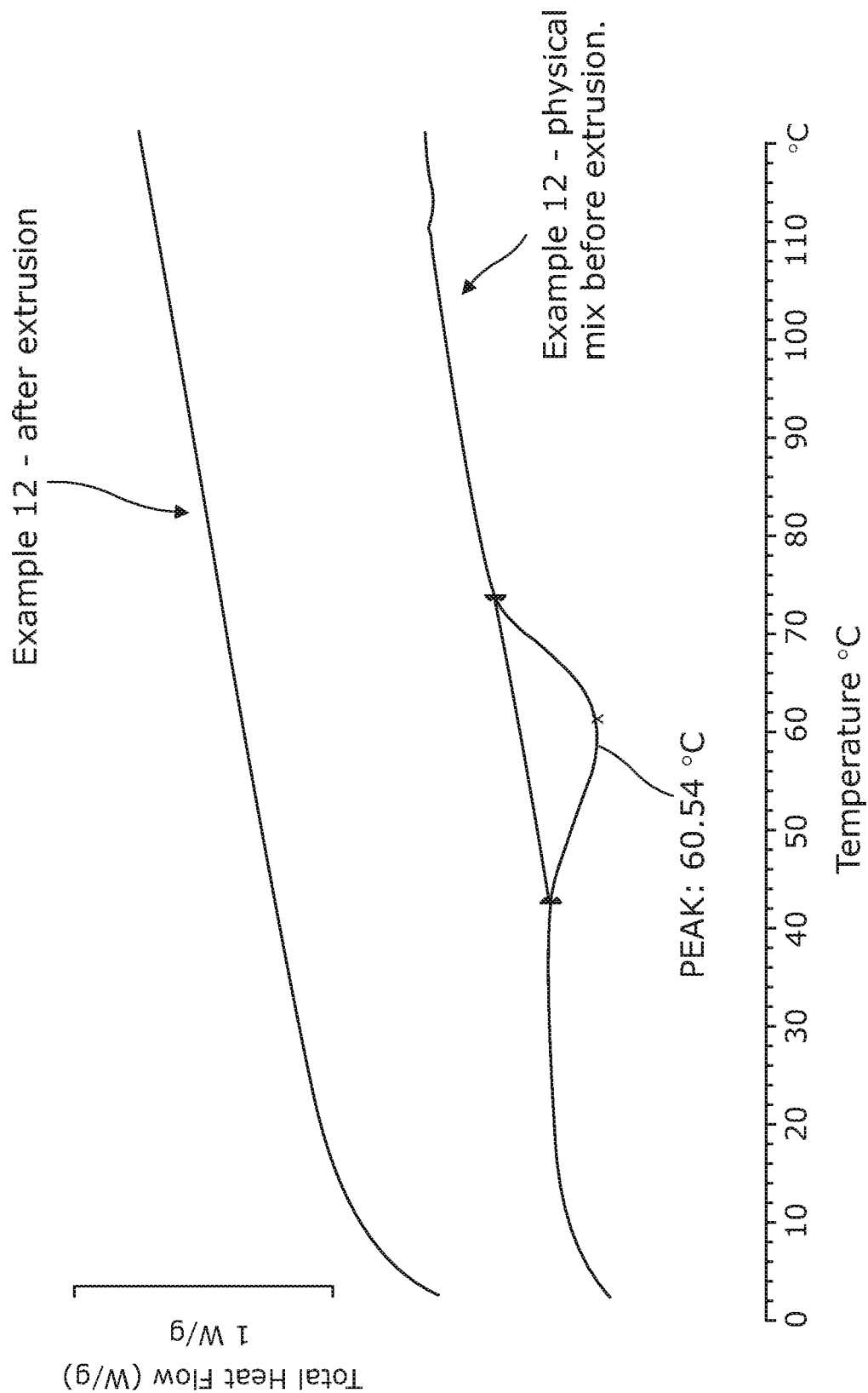
FIG. 8 shows the DSC trace for the physical mix of Example 12, and the trace for the mixture after extrusion.

FIG. 8 shows the DSC trace for the physical mix of Example 12, and the trace for the mixture after extrusion. Example 12 contains Transcutol (RIM), diethylene glycol monoethyl ether as a solubilizer. The pre-extrusion trace shows (by comparison with FIG. 7) that the presence of the solubilizer reduces the effective melting temperature of the ibuprofen from about 76.7° C. to about 60.5° C. After extrusion, no clear melting temperature is evident in the DSC trace, indicating that the ibuprofen is present in an amorphous form.

Figure 9:
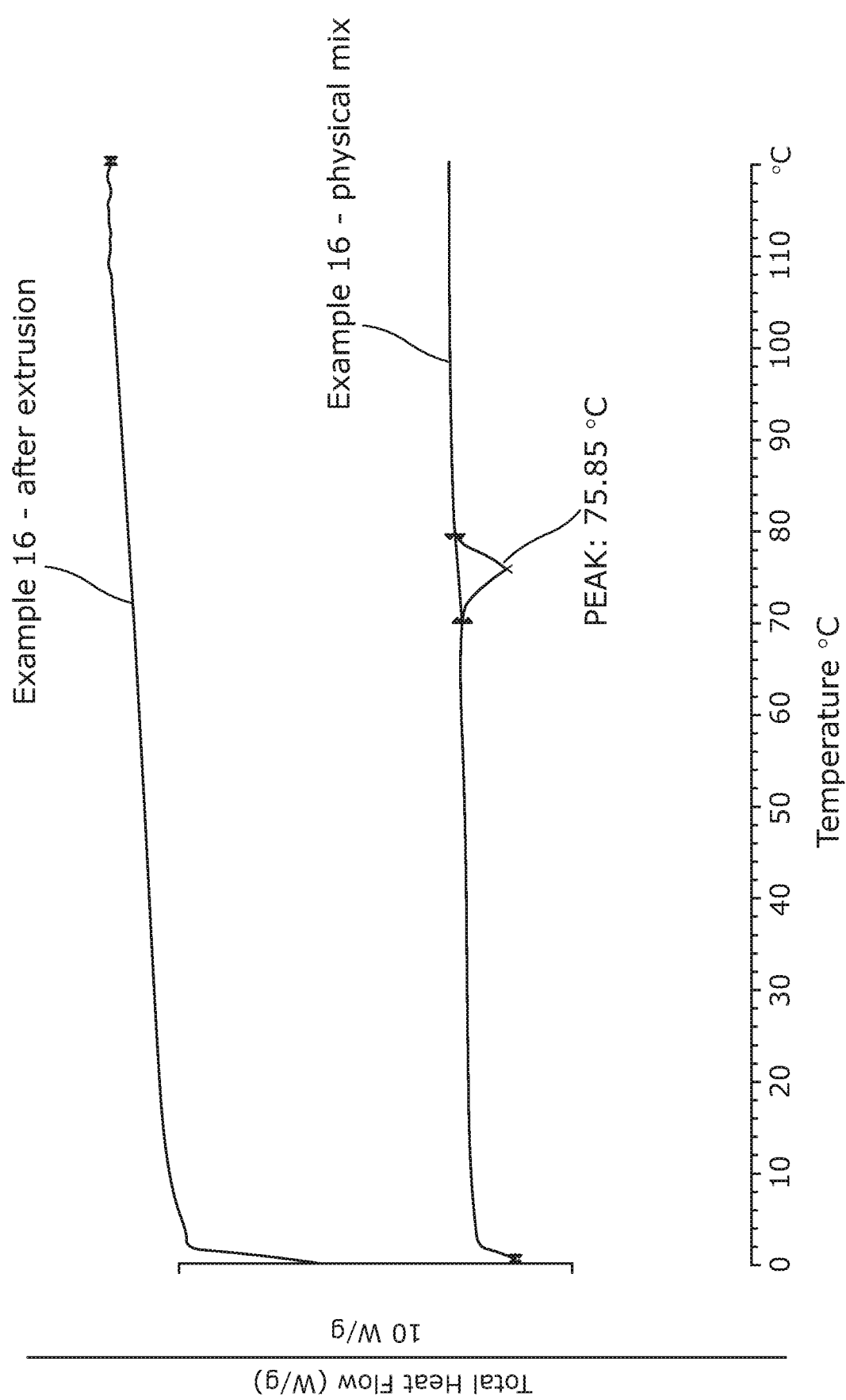
FIG. 9 shows the DSC trace for the physical mix of Example 16, and the trace for the mixture after extrusion.
Figure 10:
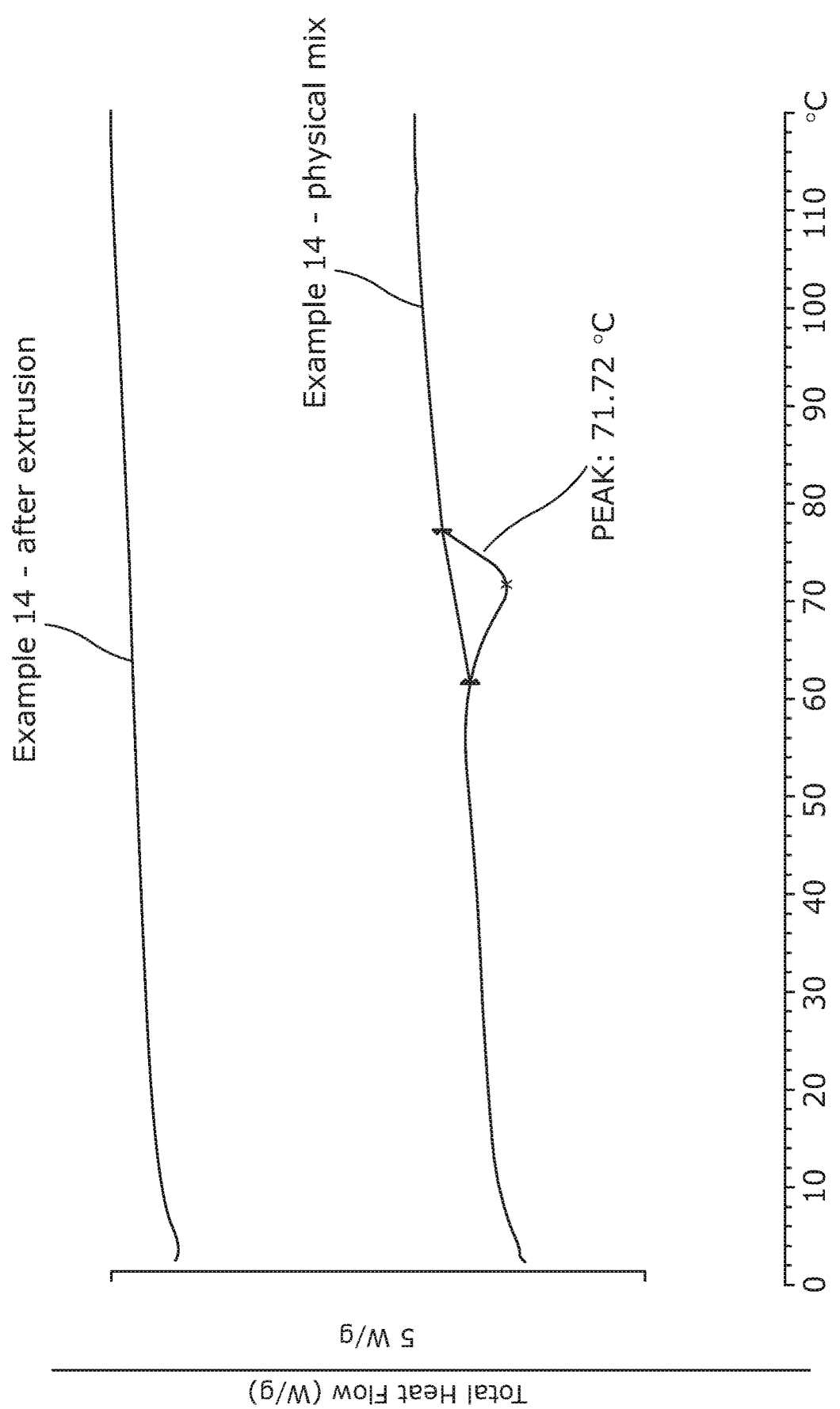
FIG. 10 shows the DSC trace for the physical mix of Example 14, and the trace for the mixture after extrusion.

FIGS. 9 and 10 show corresponding traces for Examples 16 and 14 respectively, again showing the depression of melting point by the action of the solubilizer in the pre-extrusion physical mix, and the amorphous nature of the ibuprofen following extrusion.

Figure 11:
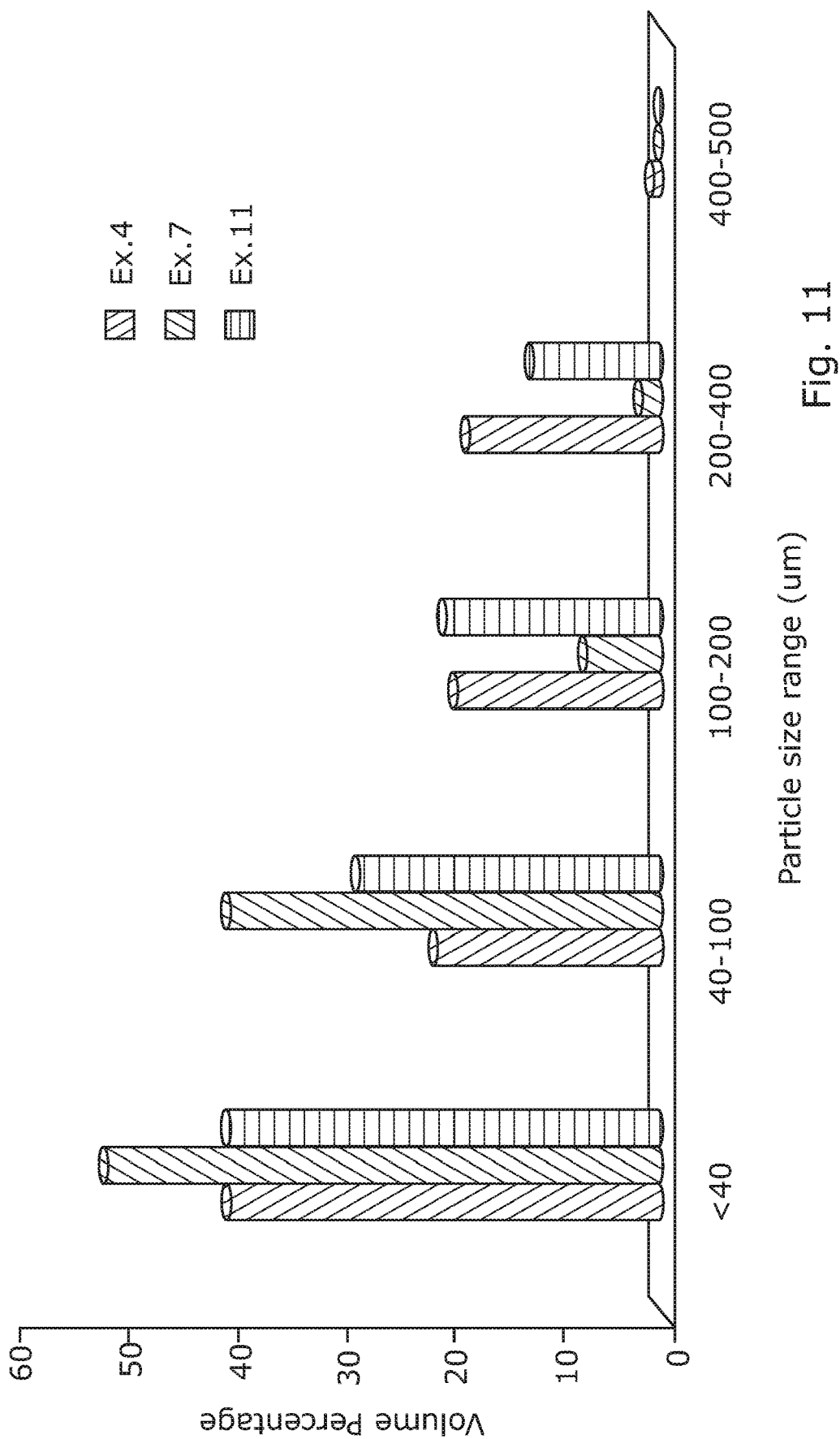
FIG. 11 shows the particle size analysis (by sieve measurement) of the extrudates obtained from the process (without further particle size reduction) for examples 4, 7 and 11.

FIG. 11 shows the particle size analysis (by sieve measurement) of the extrudates obtained from the process (without further particle size reduction) for examples 4, 7 and 11.

In vitro dissolution studies were also carried out at 1.2 on the example products, and compared to a commercially available ibuprofen formulation sold under the Registered Trademark Nurofen Meltlets.

In vitro dissolution studies were carried out in 900 ml of 0.1 M hydrochloric acid with a pH 1.2 for 2 hr using a Varian 705 DS dissolution paddle apparatus USP II (Varian Inc. North Carolina, US) at 100 rpm and 37±0.5° C. At predetermined time intervals samples were withdrawn for HPLC assay. All dissolution studies were performed in triplicate.

The amount of ibuprofen released from tablets was determined by HPLC. Agilent Technologies system equipped with a HICROM S50DS2, 5 μm×150 mm×4 mm column at 214 mm was used for the IBU RPLC assay. The mobile phase consisted of acetonitrile/water (1% acetic acid) (65: 35:0.1, v/v). The flow rate was set at 1.5 ml/min. The IBU calibration curves was constructed using a concentrations range varying from 10 μg/ml to 50 μg/ml with 20 μl injection volume.

Figure 12:
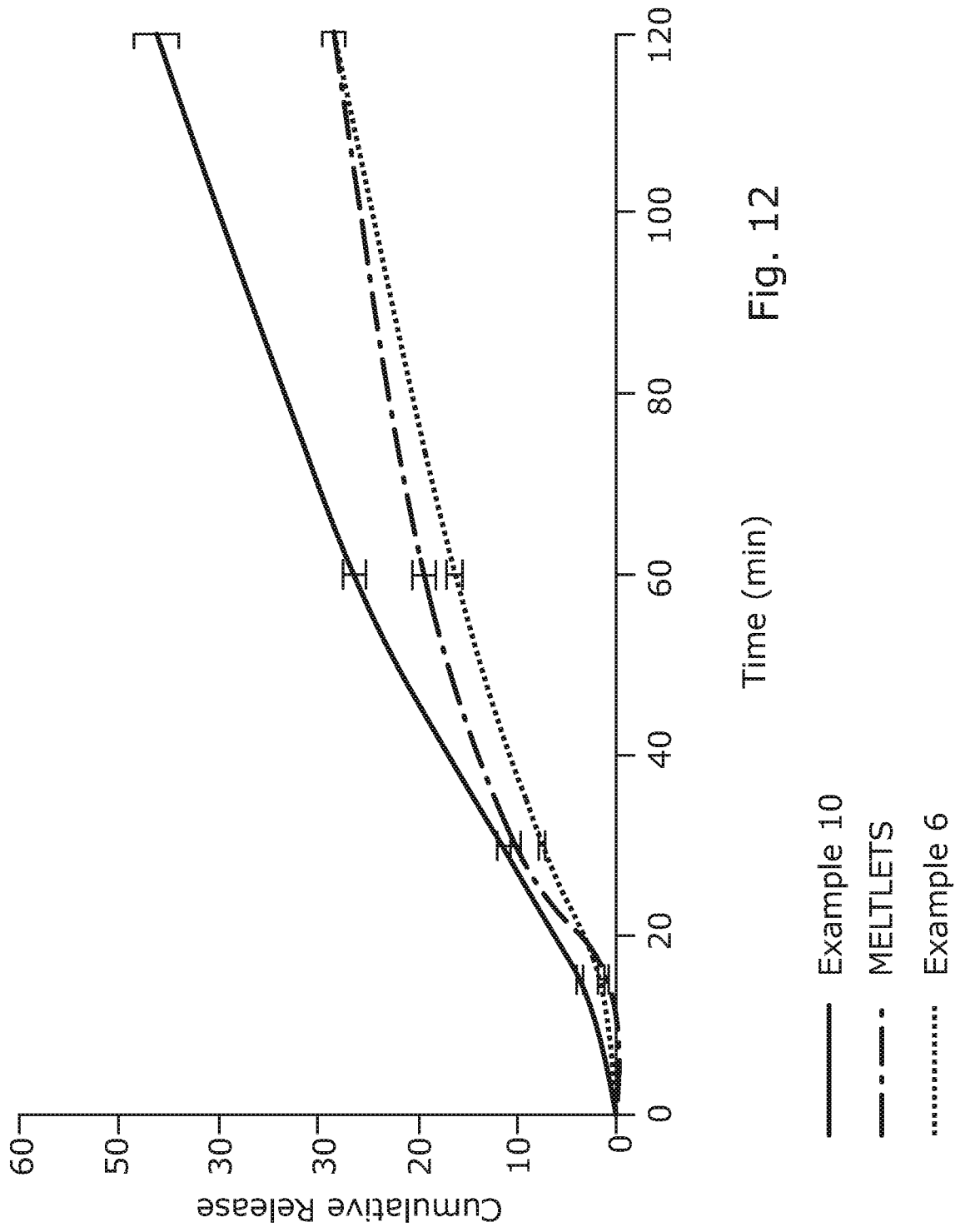
FIG. 12 shows the results from dissolution studies for Examples 10 and 6, vs. the results for the commercial Nurofen Meltlet product.

FIG. 12 shows the results from these studies for Examples 10 and 6, vs. the results for the commercial Nurofen Meltlet product. It can be seen that the initial dissolution rate (over the first 10 minutes) for the poorly water-soluble ibuprofen has been considerably increased compared to that seen in the Mallets product. This initial dissolution rate is particularly important for production of a fast-acting formulation. Example 10 is formulated as an ODT (orally dispersible tablet) and provides a consistently faster dissolution rate by comparison to the commercial Meltlets product.

Example B—Indomethacin

Further examples of the invention are presented, using indomethacin (indomethacin) as an alternative API.

For each example extrusion, Indomethacin powder was mixed thoroughly with the other ingredients for 10 minutes using a Turbula TF2 mixer (Basel, Switzerland) to form a homogeneous blend prior to processing.

In all examples, the resultant blends were extruded using an extruder barrel temperature profile of 50° C.-120° C.-170° C.-180° C.-180° C.-180° C.-180° C.-180° C. from the inlet feed to the die.

Extrusion was carried out using a screw speed of 100 to 150 rpm and a feed rate of 4-5 kg/hr. In all cases a EuroLab 16 twin screw extruder (ThermoFisher, Germany) was used. Extrudates were collected as free-flowing powders (directly from the barrel, without passing through a die).

Tablet batches were prepared using batch sizes of 100 g. All powdered/granulated extrudates were passed through a mesh sieve with an aperture of 500 μm before use. The batches were blended in a Turbula TF2 mixer (Basel, Switzerland) for 10 minutes. Routine experimentation can be used to determine appropriate mixing regimes for particular formulations used, or where the process is scaled up. Blends were directly compressed on a Flexitab trilayer tablet press (Oystar—Manesty, Germany) using 13 mm normal flat punches. Dwell time was set at 30 ms and the compaction force varied from 8-12 KN to obtain tablets of about 3 mm thickness (average weight 600 to 630 mg). The tablets were further evaluated to characterise their properties. Please note that all prepared tablets were stable under ICH (International Conference on Harmonisation of Technical Requirements for Registration of Pharmaceuticals for Human Use) storage conditions and showed effective taste masking. The tablets showed particularly high hardness, low friability and rapid disintegration times.

All prepared tablets were evaluated for the uniformity of thickness, hardness (Erweka. TBH 28, Frankfurt, Germany), friability (Erweka friabilator, model A3R, Frankfurt, Germany), and in vitro disintegration time.

In vitro disintegration time was measured for 6 tablets by inserting disks using 900 ml purified water at 37±2° C. in Disintegration Apparatus (Erweka, model ZT4, Heusenstamm, Germany) according, to USP 27 NF 22 test. (United States Pharmacopoeia, National Formulary).

In vivo disintegration was performed by a panel of 6 healthy human volunteers from whom written consent was first obtained. The study is in accordance to the Code of Ethics of the World Medical Association (Declaration of Helsinki). The healthy volunteers of either sex (age 18-25) were selected, trained and the one tablet was held in the mouth after rinsing and the time required for complete disintegration of the tablet was recorded. The time when the tablet placed on the tongue disintegrated without leaving any lumps was taken as the end point.

Six formulations (labelled IN-E1 to IN-E6) of extrudates were produced, using different concentrations of indomethacin and two different inorganic excipients, as follows:

| Ingredients | IN-E1 (w/w %) | IN-E2 (w/w %) | IN-E3 (w/w %) | IN-E4 (w/w %) | IN-E5 (w/w %) | IN-E6 (w/w %) |
|---|---|---|---|---|---|---|
| INM | 20 | 30 | 40 | 20 | 30 | 40 |
| MAS | 80 | 70 | 60 | — | — | — |
| DCPA | — | — | — | 80 | 70 | 60 |

INM: indomethacin
MAS: amorphous form of Magnesium Alumino-metasilicate ($Al_2O_3 \cdot MgO \cdot 1.7SiO_2 \cdot xH_2O$)
DCPA: diasic calcium phosphate (anhydrous) - ($CaHPO_4$)

These Extrudates (IN-E1 to IN-E6) were produced as described above, and two of them (IN-E2 and IN-E3) were used to produce twelve tablets (IN-T1 to IN-T12) with the following compositions;

| Tablet weight 250 mg | | | | |
|---|---|---|---|---|
| Excipients* | IN-T1 (w/w %) | IN-T2 (w/w %) | IN-T3 (w/w %) | IN-T4 (w/w %) |
| IN-E3 | 50 | 50 | 50 | 50 |
| XL | 10 | 12 | 15 | 20 |
| Starlac (RTM) | 12.5 | 15 | 10 | 12.5 |
| MCC | 26.3 | 21.8 | 23.8 | 16.3 |
| PRUV | 1 | 1 | 1 | 1 |
| $SiO_2$ | 0.2 | 0.2 | 0.2 | 0.2 |

| Tablet weight 335 mg | | | | |
|---|---|---|---|---|
| Excipients | IN-T5 (w/w %) | IN-T6 (w/w %) | IN-T7 (w/w %) | IN-T8 (w/w %) |
| IN-E2 | 50 | 50 | 50 | 50 |
| XL | 10 | 12 | 10 | 20 |
| Starlac (RTM) | 12.5 | 10 | 15 | 10 |
| MCC | 26.3 | 26.8 | 23.8 | 18.8 |
| PRUV | 1 | 1 | 1 | 1 |
| $SiO_2$ | 0.2 | 0.2 | 0.2 | 0.2 |

| Tablet weight 500 mg | | | | |
|---|---|---|---|---|
| Excipients* | IN-T9 (w/w %) | IN-T10 (w/w %) | IN-T11 (w/w %) | IN-T12 (w/w %) |
| IN-E3 | 50 | 50 | 50 | 50 |
| XL | 10 | 10 | 15 | 15 |
| Starlac (RTM) | 12.5 | 15 | 15 | 10 |
| MCC | 26.3 | 23.8 | 18.8 | 23.8 |
| PRUV | 1 | 1 | 1 | 1 |
| $SiO_2$ | 0.2 | 0.2 | 0.2 | 0.2 |

*Excipient Key
XL: Polyvinylpolypyrrolidone (crospovidone). This is a highly cross-linked modification of polyvinylpyrrolidone, and is used as a disintegrant.
Starlac: This is a spray-dried compound consisting of 85% alpha-lactose monohydrate (Ph. Eur./USP-NF) and 15% maize starch (Ph. Eur./USP-NF) dry matter. It increases disintegration rates, and improves flowability.

Three of the example tablet formulations were characterised for compression force, hardness, friability and disintegration, both in vivo and in vitro. The results were as follows:

| Formulation | Compression force (KN) | Hardness (Kp) | Friability (%) | Disintegration Time (s) In vivo | In vitro |
|---|---|---|---|---|---|
| IN-T1 | 10 | 8.8 | 0.5 | 14 | 10 |
| IN-T5 | 5 | 6.3 | 0.7 | 11 | 9 |
| IN-T9 | 4 | 5.3 | <0.1 | 12 | 9.4 |

Figure 13:
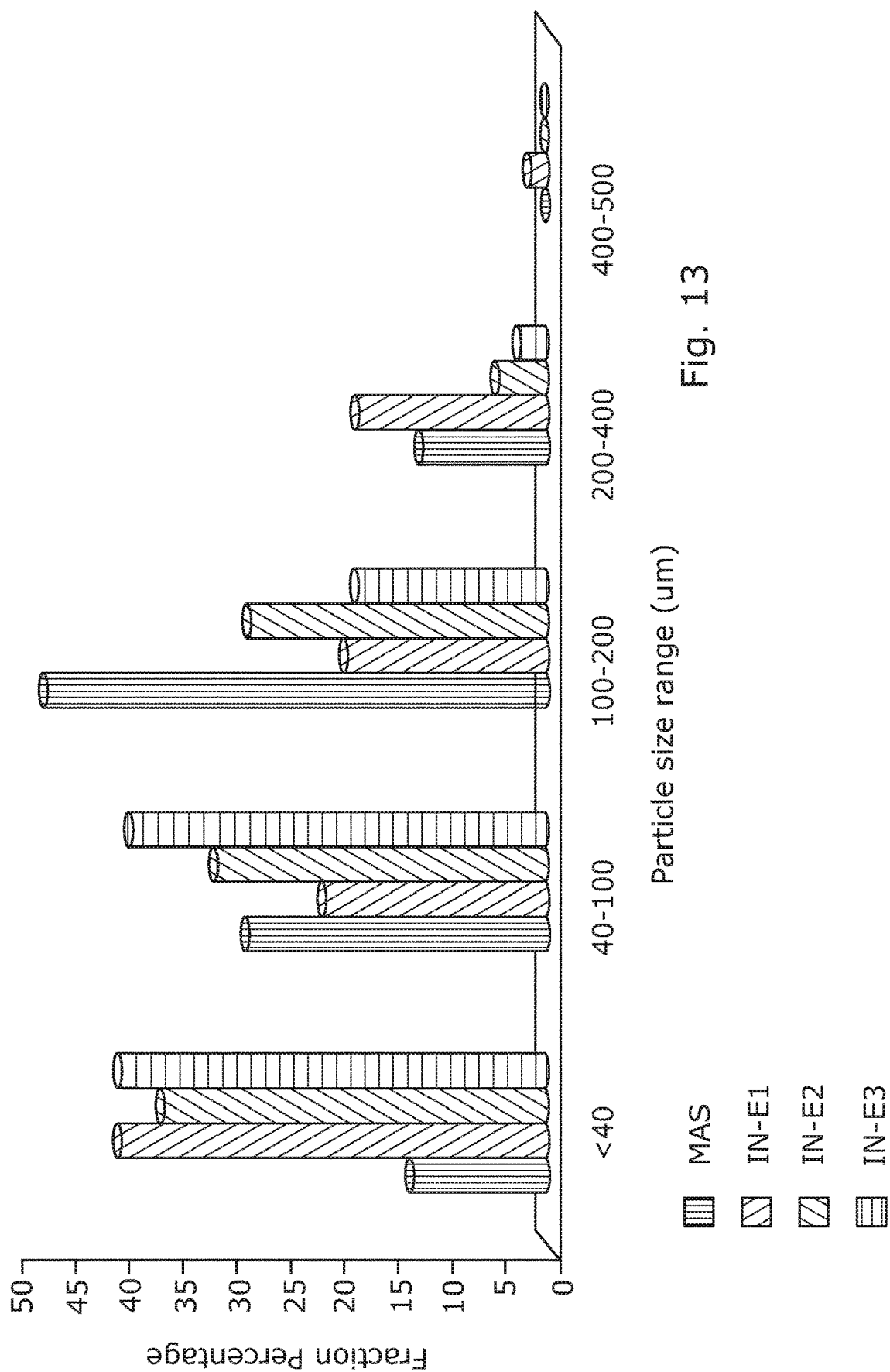
FIG. 13 shows particle size distribution results for the MAS inorganic excipient and extrudates IN-E1, IN-E2 and IN-E3.
Figure 14:
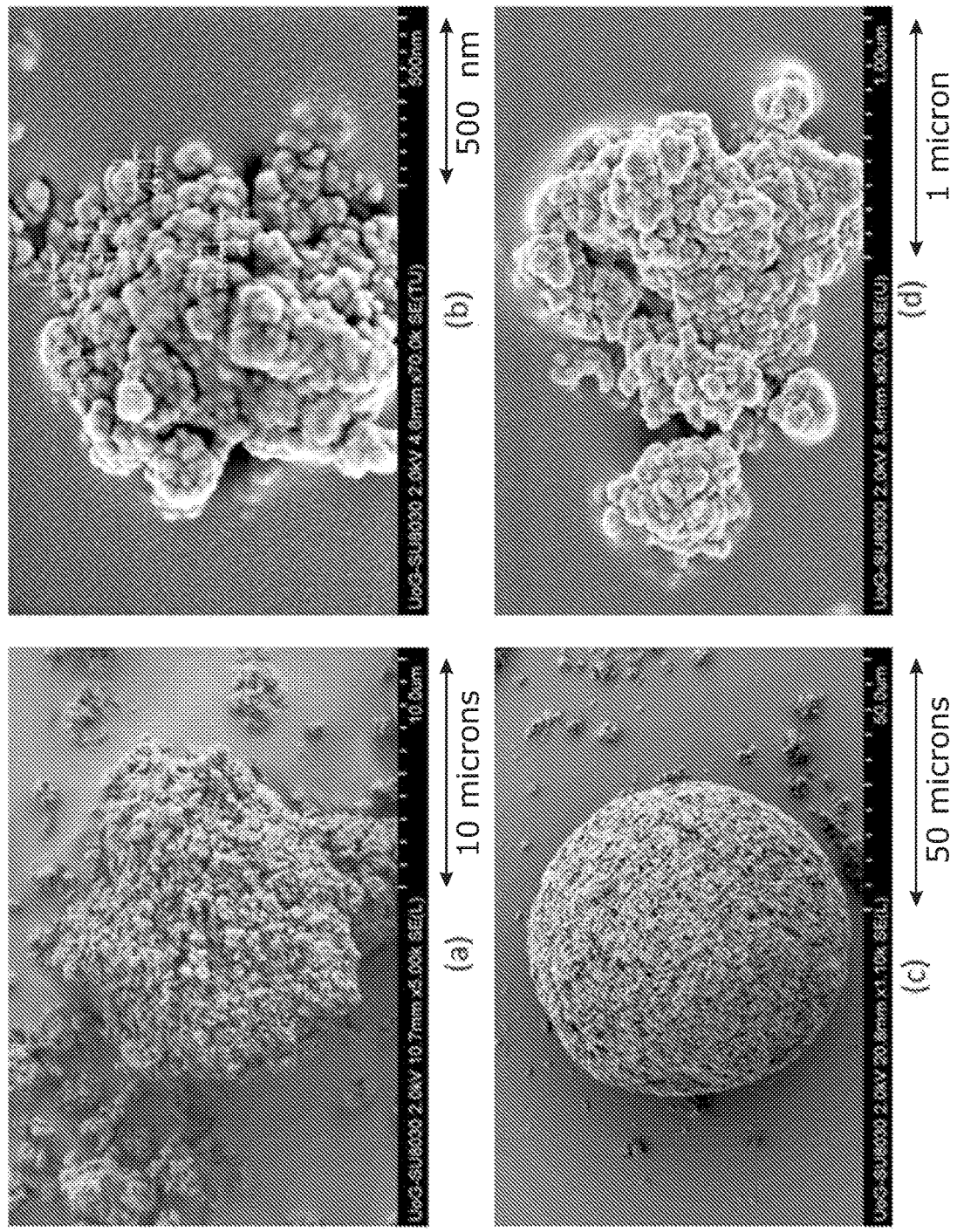
FIGS. 14(a)-(d) show Scanning Electron Micrographs images of an example extrudak at various resolutions.

The powder extrudates formed by the process were characterised as follows:

The particle size distribution of the powder extrudates was measured by sieve analysis, and example distributions for the MAS inorganic excipient and extrudates IN-E1, IN-E2 and IN-E3 are shown in FIG. 13.

Scanning Electron Micrographs were also prepared of an example extrudate, and these are shown at various resolutions in FIG. 14(a)-(d). It can be clearly seen that the powder is in the form of a granule, formed from particles of inorganic excipient, stuck together by the indomethacin.

Figure 15:
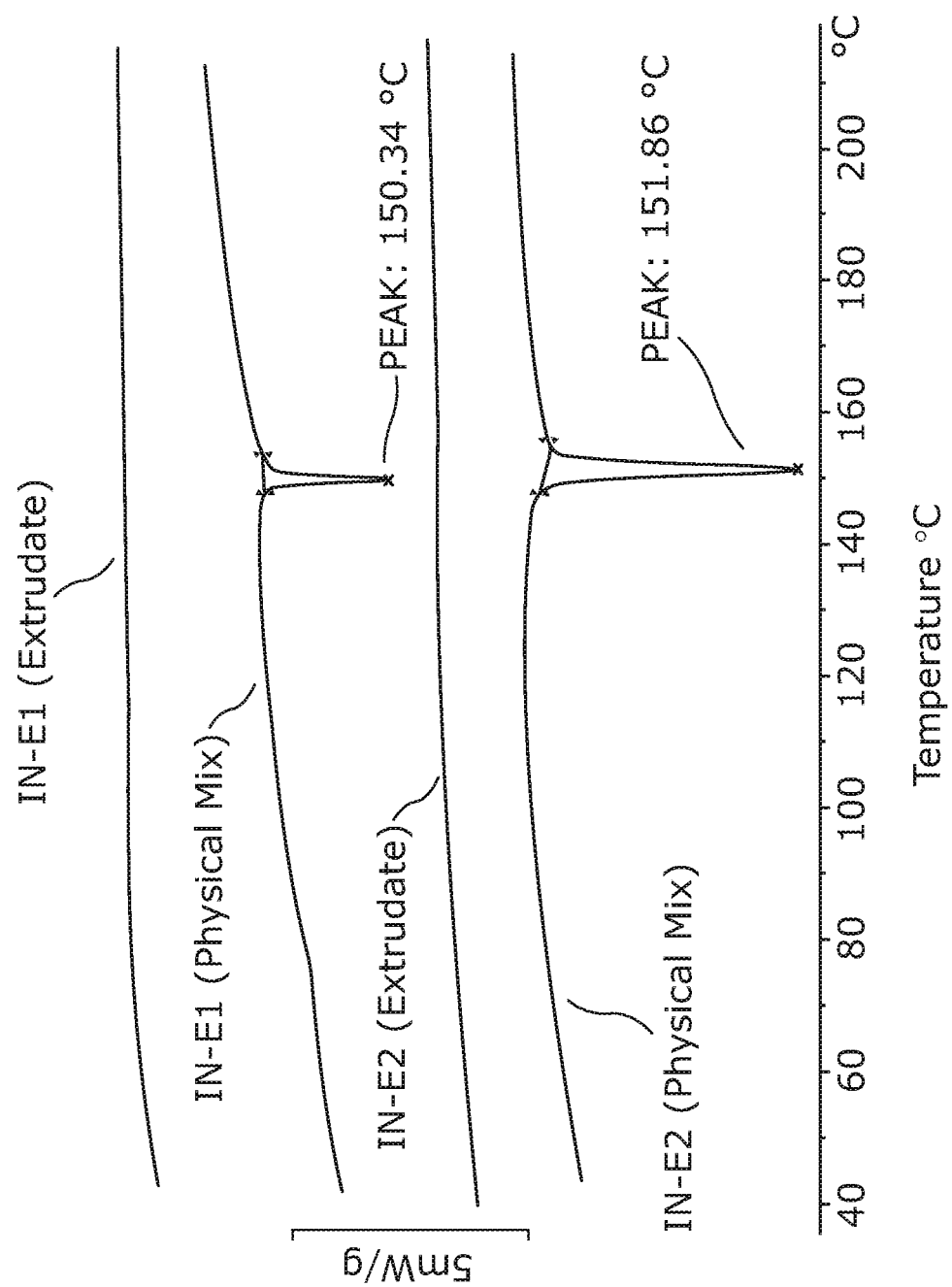
FIG. 15 shows DSC traces for the physical mixture of examples IN-E1 and IN-E2, and the trace for the mixture after extrusion.

Differential Scanning calorimetry (DSC) was also carried out on the powder extrudates, and DSC traces for examples IN-E1 and IN-E2 are shown in FIG. 15. The traces are shown for the physical mixtures before extrusion and for the powder extrudates. As was seen in the ibuprofen examples, this shows that the indomethacin, after extrusion, is amorphous, as the characteristic melting point peak is absent after extrusion.

Figure 16:
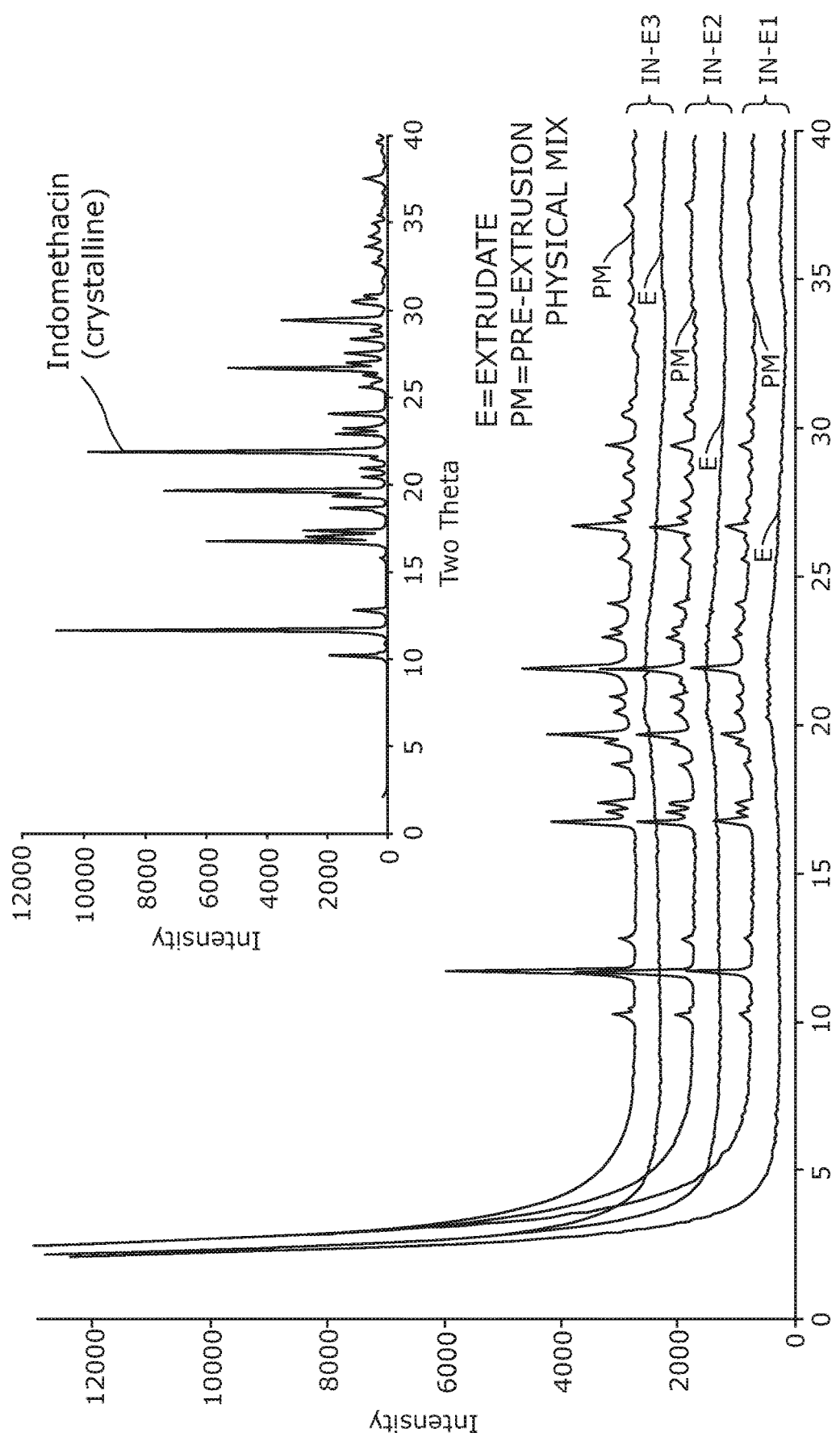
FIG. 16 shows XRPD diffractograms tar examples IN-E1, IN-E2 and IN-E3, as well as pure indomethacin.

The powder extrudates were also examined by X-Ray Powder Diffraction (XRPD) to determine the state of the indomethacin before and after extrusion. FIG. 16 shows the results for examples IN-E1, IN-E2 and IN-E3, and further demonstrates the loss of crystallinity on processing. The XRPD diffractogram for pure indomethacin is shown for reference.

Figure 17:
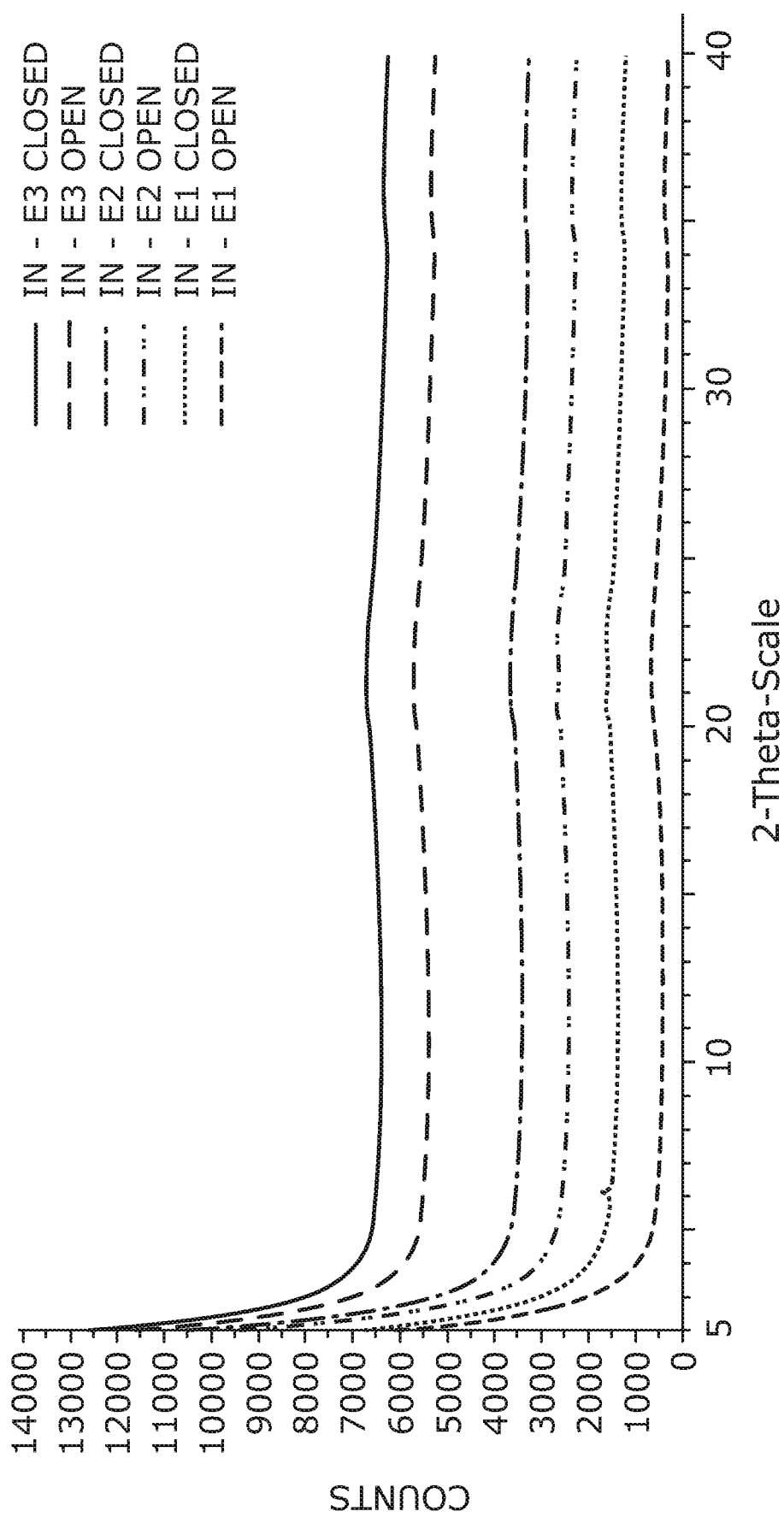
FIG. 17 shows XRPD diffractograms of three of the example extrudates (IN-E1, IN-E2 and IN-E3) after storage for six months under accelerated conditions (40° C. and 75% relative humidity), either open to the atmosphere, or in sealed containers.

Stability trials were also carried out on indomethacin-containing powder extrudates. FIG. 17 shows XRPD diffractograms of three of the example extrudates (IN-E1, IN-E2 and IN-E3) after storage for six months under accelerated conditions (40° C. and 75% relative humidity), either open to the atmosphere, or in sealed containers. The results demonstrate that there was no crystallisation of the indomethacin over this, period.

It is known that amorphous forms of compounds generally exhibit higher dissolution rates than their crystalline counterparts.

The invention claimed is:

1. A method of producing a powdered/granulated composition comprising an active pharmaceutical ingredient (API), said method comprising the steps of:
   (a) providing an API;
   (b) providing a porous and particulate inorganic excipient selected from the group consisting of dibasic calcium phosphate anhydrous (DCPA); and a metal alumina-silicate; and
   (c) processing (a) and (b) by a twin screw extrusion granulation process in a twin screw extruder without an extrusion die and in the absence of any polymer to cause absorption of the API into the pores of the inorganic excipient in an amorphous form and directly produce the powdered/granulated composition at an exit of a barrel of the twin screw extruder without cutting, wherein the powdered/granulated composition comprises the API in an amorphous form and the API is absorbed within the pores of the inorganic excipient and wherein less than 15% of the API in the powdered/granulated composition is crystalline.

2. A method according to claim 1 wherein step (c) comprises partially or fully melting the API.

3. A method according to claim 2, wherein step (c) is carried out in the absence of a solvent.

4. A method according to claim 1 wherein the method further comprises partially or fully solubilising the API in a solubiliser.

5. A method according to claim 4, wherein step (c) is carried out in the absence of heating.

6. A method according to claim 1, wherein the API is hydrophobic.

7. A method according to claim 6 wherein the API has a water solubility of 20 mg/ml or less.

8. A method according to claim 7 wherein the API is selected from the list consisting of: Ibuprofen, Indomethacin, Lamotridine, Diazepam, Griseofulvin, Progesterone, 17 beta-estradiol, Furosemide, Gliclazide, Glipizide, Aceclofenac, Ketoprofen, Diclofenac, Felodipine, Morphine, Naproxone, Nimodipine, Ofloxacin, Curcumin, Paclitaxel, and Cisplatin.

9. A method according to claim 1, wherein the inorganic excipient has a specific surface area of more than 200 $m^2/g$.

10. A method according to claim 1, wherein the inorganic excipient has a Carr Index of less than 18.

11. A method according to claim 1 wherein the inorganic excipient is Magnesium Alumino-metasilicate ($Al_2O_3MgO.1.7SiO_2.xH_2O$).

12. A method of producing a powdered/granulated composition comprising an active pharmaceutical ingredient (API), said method comprising the steps of:

(a) providing an API;
(b) providing a porous and particulate inorganic excipient selected from the group consisting of dibasic calcium phosphate anhydrous (DCPA); and a metal aluminasilicate;
(c) processing (a) and (b) by a twin screw extrusion granulation process in a twin screw extruder without an extrusion die, in the absence of any polymer, and without cutting to cause absorption of the API into the pores of the inorganic excipient in an amorphous form directly produce a powdered/granulated composition, wherein the powdered/granulated composition comprises the API in an amorphous form, wherein the API is absorbed within the pores of the inorganic excipient and wherein less than 15% of the API in the powdered/granulated composition is crystalline;
(d) blending the powdered/granulated composition with one or more pharmaceutically acceptable excipients to produce a composition blend; and
(e) directly compressing the composition blend into a direct compression tablet.

13. A powdered/granulated composition obtainable by a method of claim 1.

14. A method according to claim 4, wherein the solubilizer is selected from the group consisting of: glycerides, fatty acids, fatty alcohols, glycols and derivatives thereof.

15. A method according to claim 1, wherein step (c) is performed at a temperature below the melting point of the API of (a).

16. A method according to claim 1, wherein the inorganic excipient is present in an amount of at least 45% w/w.

* * * * *